(12) United States Patent
Böhm et al.

(10) Patent No.: US 8,603,024 B2
(45) Date of Patent: Dec. 10, 2013

(54) GLAUCOMA DRAINAGE DEVICES INCLUDING VARIO-STABLE VALVES AND ASSOCIATED SYSTEMS AND METHODS

(75) Inventors: Sebastian Böhm, San Diego, CA (US); Leslie A. Field, Portola Valley, CA (US); Matthew J. A. Rickard, Yorba Linda, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

(21) Appl. No.: 13/316,717

(22) Filed: Dec. 12, 2011

(65) Prior Publication Data

US 2013/0150776 A1    Jun. 13, 2013

(51) Int. Cl.
*A61M 5/00* (2006.01)

(52) U.S. Cl.
USPC .................................... 604/9; 606/4

(58) Field of Classification Search
USPC .......................... 604/8, 9; 606/4–6
See application file for complete search history.

(56) References Cited

U.S. PATENT DOCUMENTS

| | | |
|---|---|---|
| 4,089,329 A | 5/1978 | Couvillon et al. |
| 4,206,762 A | 6/1980 | Cosman |
| 4,457,757 A | 7/1984 | Molteno |
| 4,656,827 A | 4/1987 | Puillet |
| 4,750,901 A | 6/1988 | Molteno |
| 4,922,913 A | 5/1990 | Waters et al. |
| 5,005,577 A | 4/1991 | Frenkel |
| 5,178,604 A | 1/1993 | Baerveldt |
| 5,179,953 A | 1/1993 | Kursar |
| 5,397,300 A | 3/1995 | Baerveldt |
| 5,476,445 A | 12/1995 | Baerveldt |
| 5,558,629 A | 9/1996 | Baerveldt |
| 5,910,110 A | 6/1999 | Bastable |
| 6,007,511 A | 12/1999 | Prywes |
| 6,447,449 B1 | 9/2002 | Fleischman et al. |
| 6,468,283 B1 | 10/2002 | Richter et al. |
| 6,579,235 B1 | 6/2003 | Abita et al. |
| 6,589,198 B1 | 7/2003 | Soltanpour et al. |

(Continued)

FOREIGN PATENT DOCUMENTS

| | | |
|---|---|---|
| DE | 4438201 | 5/1996 |
| EP | 2427097 | 3/2012 |

(Continued)

OTHER PUBLICATIONS

Byunghoon Bae, Hongseok Kee, Seonho Kim, Yeon Lee, Taeseok Sim, Yongkweon Him and Kyihwan Park; "In Vitro Experiment of the Pressure Regulating Valve for a Glaucoma Impact"; Journal of Micromechanics and Microengineering, 13 (2003); pp. 613-619.

(Continued)

*Primary Examiner* — Melanie Hand
(74) *Attorney, Agent, or Firm* — Kenneth D. Bassinger

(57) ABSTRACT

Glaucoma drainage devices including vario-stable valves and associated systems and methods are disclosed. A glaucoma drainage device includes a drainage lumen and a valve system coupled to the drainage lumen to control the flow of fluid through the drainage lumen. The valve system includes an adjustable valve with a diaphragm that is in communication with the drainage lumen and is movable to occupy varying amounts of the drainage lumen. In some embodiments, the valve system is maintained in a desired position without the use of power such that power is only needed when changing a position of the adjustable valve.

20 Claims, 13 Drawing Sheets

(56) References Cited

U.S. PATENT DOCUMENTS

| | | |
|---|---|---|
| 6,682,500 B2 | 1/2004 | Soltanpour et al. |
| 6,712,764 B2 | 3/2004 | Jeffries et al. |
| 6,749,568 B2 | 6/2004 | Fleischman et al. |
| 6,939,299 B1 | 9/2005 | Petersen et al. |
| 7,137,952 B2 | 11/2006 | Leonardi et al. |
| 7,169,106 B2 | 1/2007 | Fleischman et al. |
| 7,252,006 B2 | 8/2007 | Tai et al. |
| 7,354,416 B2 | 4/2008 | Quiroz-Mercado et al. |
| 7,409,863 B2 | 8/2008 | Bateman et al. |
| 7,612,328 B2 | 11/2009 | Kaiser |
| 8,182,435 B2 | 5/2012 | Dacquay et al. |
| 8,257,295 B2 | 9/2012 | Rickard et al. |
| 2001/0000527 A1 | 4/2001 | Yaron et al. |
| 2002/0019607 A1 | 2/2002 | Bui |
| 2002/0049374 A1 | 4/2002 | Abrea |
| 2002/0099359 A1 | 7/2002 | Santini, Jr. et al. |
| 2002/0143284 A1 | 10/2002 | Tu et al. |
| 2002/0193674 A1 | 12/2002 | Fleischmann et al. |
| 2003/0078487 A1 | 4/2003 | Jeffries |
| 2003/0225318 A1 | 12/2003 | Montegrande et al. |
| 2004/0059248 A1 | 3/2004 | Messner et al. |
| 2004/0073137 A1 | 4/2004 | Lloyd et al. |
| 2004/0111050 A1 | 6/2004 | Smedley et al. |
| 2004/0116794 A1 | 6/2004 | Fink et al. |
| 2004/0186367 A1 | 9/2004 | Fresco |
| 2004/0254438 A1 | 12/2004 | Chuck et al. |
| 2004/0254517 A1 | 12/2004 | Quiroz-Mercado et al. |
| 2005/0159660 A1 | 7/2005 | Montegrande et al. |
| 2005/0271704 A1 | 12/2005 | Tu et al. |
| 2005/0273033 A1 | 12/2005 | Grahn et al. |
| 2006/0131350 A1 | 6/2006 | Schechter et al. |
| 2007/0019156 A1 | 1/2007 | Fink |
| 2007/0032757 A1 | 2/2007 | Medow et al. |
| 2007/0106199 A1 | 5/2007 | Krivoy et al. |
| 2007/0109117 A1 | 5/2007 | Heitzmann et al. |
| 2007/0123767 A1 | 5/2007 | Montegrande et al. |
| 2007/0129623 A1 | 6/2007 | Fleischman et al. |
| 2007/0212397 A1 | 9/2007 | Roth |
| 2008/0015421 A1 | 1/2008 | Penner |
| 2008/0077127 A1 | 3/2008 | Gao et al. |
| 2008/0125691 A1 | 5/2008 | Yaron et al. |
| 2008/0129486 A1 | 6/2008 | Jeckelmann et al. |
| 2008/0228127 A1 | 9/2008 | Burns et al. |
| 2009/0069648 A1 | 3/2009 | Irazqui et al. |
| 2009/0076367 A1 | 3/2009 | Sit et al. |
| 2009/0143713 A1 | 6/2009 | Van Dam et al. |
| 2009/0227933 A1 | 9/2009 | Karageozian |
| 2009/0275924 A1 | 11/2009 | Latanzio et al. |
| 2009/0312742 A1 | 12/2009 | Pang et al. |
| 2010/0010416 A1 | 1/2010 | Juan, Jr. et al. |
| 2010/0042209 A1 | 2/2010 | Guarnieri |
| 2010/0121348 A1 | 5/2010 | Van Der Burg et al. |
| 2010/0234717 A1 | 9/2010 | Wismer |
| 2010/0253167 A1 | 10/2010 | Charnley et al. |
| 2011/0046536 A1 | 2/2011 | Stegmann et al. |
| 2011/0071454 A1 | 3/2011 | Santos et al. |
| 2011/0071456 A1 | 3/2011 | Rickard |
| 2011/0071458 A1* | 3/2011 | Rickard .................... 604/9 |
| 2011/0248671 A1 | 10/2011 | Santos et al. |

FOREIGN PATENT DOCUMENTS

| | | |
|---|---|---|
| WO | WO 93/03665 | 3/1993 |
| WO | WO 98/03665 | 1/1998 |
| WO | WO 99/38470 A2 | 8/1999 |
| WO | WO 99/38470 A3 | 10/1999 |
| WO | WO 01/94784 | 12/2001 |
| WO | WO 03/001991 | 1/2003 |
| WO | WO 03/102632 | 12/2003 |
| WO | WO 2007/127305 A2 | 11/2007 |
| WO | WO 2007/136993 | 11/2007 |
| WO | WO 2008/061043 A2 | 5/2008 |
| WO | WO 2008/061043 A3 | 9/2008 |
| WO | WO 2009/026499 | 2/2009 |
| WO | WO 2009/049686 | 4/2009 |
| WO | WO 2009/081031 | 7/2009 |
| WO | WO 2009/081031 A3 | 9/2009 |
| WO | WO 2011/034727 A1 | 3/2011 |
| WO | WO 2011/034738 A1 | 3/2011 |
| WO | WO 2011/034740 A1 | 3/2011 |
| WO | WO 2011/034742 A2 | 3/2011 |
| WO | WO 2011/035218 A1 | 3/2011 |
| WO | WO 2011/034742 A3 | 5/2011 |

OTHER PUBLICATIONS

Eggers, T., et al, "Wireless Intra-Ocular Pressure Monitoring System Integrated Into an Artificial Lens," 1st Annual Int'l IEEE-EMBS Special Topic Conference on Microtechnologies in Medicine & Biology, Oct. 12-14, 2000, pp. 466-469, Lyon, France.

Erik Stemme and Goran Stemme; "A Valveless Diffuser/Nozzle-Based Fluid Pump"; ScienceDirect; Sensors and Actuators A, 39 (1993); pp. 159-167.

Greene, M.E. and Gilman, B.G., "Intraocular Pressure Measurement With Instrumented Contact Lenses," Investigative Ophthalmology & Visual Science (IVOS), Apr. 1974, pp. 299-302, vol. 13, No. 4, IVOS.

Hjortdal, Jesper and Jensen, Peter, "In Vitro Measurement of Corneal Strain, Thickness, and Curvature Using Digital Image Processing," Acta Ophthalmologica Scandinavica, 1995, pp. 5-11, vol. 73, Denmark.

International Searching Authority, Search Report and Written Opinion of the International Searching Authority, PCT/US2010/033329, Jul. 13, 2010, 14 pages.

International Searching Authority, Search Report and Written Opinion of the International Searching Authority, PCT/US2010/047429, Nov. 1, 2010, 15 pages.

International Searching Authority, Search Report and Written Opinion of the International Searching Authority, PCT/US2010/047600, Dec. 14, 2010, 13 pages.

International Searching Authority, Search Report and Written Opinion of the International Searching Authority, PCT/US2010/049424, Nov. 26, 2010, 15 pages.

International Searching Authority, Search Report of the International Searching Authority, PCT/US2011/036742, Aug. 17, 2011, 2 pages.

Lam, Andrew K.C. and Douthwaite, William A., "The Effect of an Artificially Intraocular Pressure on the Central Corneal Curvature," Ophthalmic and Physiological Optics, 1997, pp. 18-24, vol. 17, No. 1, Elsevier Science, Ltd., Great Britain.

Leonardi, Matteo, et al., "A Soft Contact Lens With a Mems Strain Gage Embedded for Intraocular Pressure Monitoring," In Proc. 12th Int'l Conference on Solid State Sensors, Actuators and Microsystems, Jun. 8-12, 2003, pp. 1043-1046, vol. 2, Boston, MA.

Leonardi, Matteo, et al., "First Steps Toward Noninvasive Intraocular Pressure Monitoring with a Sensing Contact Lens," Investigative Ophthalmology & Visual Science (IVOS), 2004, pp. 3113-3117, vol. 45, No. 9, IVOS.

McLaren, Jay W., et al, "Continuous Measurement of Intraocular Pressure in Rabbits by Telemetry," Investigative Ophthalmology & Visual Science (IVOS), May 1996, pp. 966-975, vol. 37, No. 6, IVOS.

Mokwa, Wilfried, et al, "Micro-Transponder Systems for Medical Applications," IEEE Transactions on Instrumentation and Measurement, Dec. 2001, pp. 1551-1555, vol. 50, No. 6, IEEE, Germany.

Neagu Cristina R.; "A Medical Microactuator Based on an Electrochemical Principle"; Thesis at the Twente University,the Netherlands, Enschede; Aug. 28, 1998; pp. 1-162.

Nisar A., Afzulpurkar Nitin, Mahaisavariya Banchong, and Tuantranont Adisorn; "MEMS-Based Micropumps in Drug Delivery and Biomedical Applications"; ScienceDirect; Sensors and Actuators B 130 (2008) pp. 917-942.

Puers, Robert, "Linking Sensors with Telemetry: Impact on the System Design," In Proc. 8th Int'l Conference of Solid State Sensors, Actuators, Eurosens, Jun. 25-29, 1995, pp. 169-174, Stockholm, Sweden.

Saloomeh Saati MD., Ronalee Lo PhD, Po-Ying Li PhD, Ellis Meng PhD, Rohit Varma MD MPH, and Mark S. Humayun MD PhD; "Mini Drug Pump for Ophthalmic Use"; TRANS Am Ophthalmol Soc 2009; 107; pp. 60-71.

(56) References Cited

OTHER PUBLICATIONS

Schnakenberg, U., et al, "Initial Investigations on Systems for Measuring Intraocular Pressure," Sensors and Actuators, 2000, p. 287-291, vol. 85, Elsevier Science B.V., Germany.

Stangel, Karsten, et al, "A Programmable Intraocular CMOS Pressure Sensor System Implant," IEEE Journal of Solid-State Circuits, Jul. 2001, pp. 1094-1100, vol. 36, No. 7, IEEE, Germany.

Ullerich, Stella, et al, "Micro Coils for an Advanced System for Measuring Intraocular Pressure," 1st Annual Int'l IEEE-EMBS Special Topic Conference on Microtechnologies in Medicine & Biology, Oct. 12-14, 2000, pp. 470-474, Lyon, France.

Van Schuylenbergh, K., et al, "An Implantable Telemetric Tonometer for Direct Intraocular Pressure Measurements," 1st European Conference on Biomedical Engineering, Feb. 1991, pp. 194-195, vol. 17, No. 20, Nice, France.

"Walter, Peter; Intraocular Pressure Sensor: Where Are We—Where Will We Go? Journal Graefe's Archive for Clinical and Experimental Ophthalmology; Publisher Springer Berline/Heidelberg; ISSN 0721-832X (Print) 1435-702X (Online); Issue vol. 240, No. 5/May 2002 DOI 10.1007/s00417-002-0474-y; pp. 335-336; Subject Collection Medicine."

International Searching Authority, Written Opinion of the International Searching Authority, PCT/US2010/047605, Dec. 16, 2010, 9 pages.

International Searching Authority, International Search Report of the International Searching Authority, PCT/US2010/047612, Dec. 21, 2010, 7 pages.

International Searching Authority, Written Opinion of the International Searching Authority, PCT/US2010/047612, Dec. 21, 2010, 10 pages.

* cited by examiner

GLAUCOMA DRAINAGE DEVICES INCLUDING VARIO-STABLE VALVES AND ASSOCIATED SYSTEMS AND METHODS

BACKGROUND

The present disclosure relates generally to valves and associated systems and methods for use in ophthalmic treatments. In some instances, embodiments of the present disclosure are configured to be part of an IOP control system.

Glaucoma, a group of eye diseases affecting the retina and optic nerve, is one of the leading causes of blindness worldwide. Most forms of glaucoma result when the intraocular pressure (IOP) increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

The eye's ciliary body continuously produces aqueous humor, the clear fluid that fills the anterior segment of the eye (the space between the cornea and lens). The aqueous humor flows out of the anterior chamber (the space between the cornea and iris) through the trabecular meshwork and the uveoscleral pathways, both of which contribute to the aqueous drainage system. The delicate balance between the production and drainage of aqueous humor determines the eye's IOP.

FIG. 1 is a diagram of the front portion of an eye that helps to explain the processes of glaucoma. In FIG. 1, representations of the lens 110, cornea 120, iris 130, ciliary body 140, trabecular meshwork 150, and Schlemm's canal 160 are pictured. Anatomically, the anterior segment of the eye includes the structures that cause elevated IOP which may lead to glaucoma. Aqueous fluid is produced by the ciliary body 140 that lies beneath the iris 130 and adjacent to the lens 110 in the anterior segment of the eye. This aqueous humor washes over the lens 110 and iris 130 and flows to the drainage system located in the angle of the anterior chamber. The angle of the anterior chamber, which extends circumferentially around the eye, contains structures that allow the aqueous humor to drain. The trabecular meshwork 150 is commonly implicated in glaucoma. The trabecular meshwork 150 extends circumferentially around the anterior chamber. The trabecular meshwork 150 seems to act as a filter, limiting the outflow of aqueous humor and providing a back pressure that directly relates to IOP. Schlemm's canal 160 is located beyond the trabecular meshwork 150. Schlemm's canal 160 is fluidically coupled to collector channels (not shown) allowing aqueous humor to flow out of the anterior chamber. The two arrows in the anterior segment of FIG. 1 show the flow of aqueous humor from the ciliary bodies 140, over the lens 110, over the iris 130, through the trabecular meshwork 150, and into Schlemm's canal 160 and its collector channels.

One method of treating glaucoma includes implanting a drainage device in a patient's eye. The drainage device allows fluid to flow from the interior chamber of the eye to a drainage site, relieving pressure in the eye and thus lowering IOP. These devices are generally passive devices and do not provide a smart, interactive control of the amount of flow through the drainage tube. In addition, fluid filled blebs frequently develop at the drainage site. The development of the bleb typically includes fibrosis, which leads to increased flow resistance and it is generally the case that this resistance increases overtime. This development and progression of fibrosis reduces or eliminates flow from the anterior chamber, eliminating the capacity of the drainage device to affect IOP.

The system and methods disclosed herein overcome one or more of the deficiencies of the prior art.

SUMMARY

In one embodiment consistent with the principles of the present disclosure, a glaucoma drainage device is provided. The glaucoma drainage device includes a drainage lumen and a valve system coupled to the drainage lumen and optional pump. The valve system includes an adjustable valve. In some instances the adjustable valve is arranged as a boss valve, which includes a portion with a raised, thicker, and/or stiffer bossed area in some instances. The adjustable valve has a housing defining a cavity and a diaphragm bounding at least one side of the cavity. The diaphragm is in communication with the drainage lumen and is movable between a first position that occupies a first amount of the drainage lumen and a second position that occupies a second amount of the drainage lumen, where the second amount is greater than the first amount. A fluid reservoir is in fluid communication with the cavity of the adjustable valve. In that regard, a first check valve is positioned between the fluid reservoir and the cavity of the adjustable valve along a first fluid passageway. The first check valve prevents fluid flow from the fluid reservoir to the cavity of the adjustable valve. Further, a second check valve is positioned between the fluid reservoir and the cavity of the adjustable valve along a second fluid passageway. The second check valve prevents fluid flow from the cavity of the adjustable valve to the fluid reservoir.

In some instances, the valve system further includes an actuator for controlling a flow of fluid between the fluid reservoir and the cavity of the adjustable valve. In that regard, the actuator is a voltage source and a pair of electrodes in some embodiments. The pair of electrodes is positioned within the fluid reservoir in some instances. In other instances, one of the electrodes is positioned within the fluid reservoir and the other electrode is positioned outside of the fluid reservoir. In one specific instance, the second electrode is positioned within the cavity of the adjustable valve.

In some configurations, the valve system also includes a first adjustable component positioned adjacent the first fluid passageway such that a diaphragm of the first adjustable component is movable between a first position that occupies a first amount of the first fluid passageway and a second position that occupies a second amount of the first fluid passageway, where the second amount is greater than the first amount. Further, in some embodiments, the valve system further includes a second adjustable component positioned adjacent the second fluid passageway such that a diaphragm of the second adjustable component is movable between a first position that occupies a first amount of the second fluid passageway and a second position that occupies a second amount of the second fluid passageway, where the second amount is greater than the first amount. The adjustable components are bubble chambers in some implementations.

The glaucoma drainage device also includes associated pressures in some embodiments. In one embodiment, a first pressure sensor is configured for positioning in fluid communication with an anterior chamber of an eye and a second pressure sensor is configured for positioning in fluid communication with a drainage location. Readings from the first and second pressure sensors are utilized to control the actuator. In that regard, in some instances the glaucoma drainage device includes a processor in communication with the first and second pressure sensors and the actuator that processes data received from the pressure sensors to control the actuator. In some embodiments, the glaucoma drainage device includes a third pressure sensor configured for positioning within a subconjunctival space of the eye such that the third pressure sensor provides an indication of atmospheric pressure. In that regard, readings from any combination of the first, second, and third pressure sensors may be utilized to control the actuator. Note that the difference between the anterior chamber pressure sensor and the atmospheric reference pressure sensor will provide an IOP measurement that may be used for adjusting the actuator. Similarly, the difference between the absolute drainage site pressure and the atmospheric reference pressure will provide a true (gauge) reading of the drainage site pressure.

In some instances, the fluid reservoir is formed of a material that defines a constant volume cavity during operation. In other instances, the fluid reservoir is formed of a flexible material that defines a variable volume cavity during operation. In some embodiments, an electro-kinetic membrane is positioned between the fluid reservoir and the cavity of the adjustable valve. In such embodiments, an electro-kinetic fluid is received within the fluid reservoir and the cavity of the adjustable valve. In that regard, to control the flow of electro-kinetic fluid, one of the pair of electrodes is positioned on opposite sides of the membrane thereby inducing a controllable, electro-osmotic pressure gradient. In a different embodiment, the actuator comprises an actuator fluid and a bubble-generating system configured to generate bubbles by converting at least a portion of the actuator fluid to a gas.

In another embodiment consistent with the principles of the present disclosure, a valve system for use within an ophthalmological device is provided. The valve system includes an adjustable valve having a housing defining a cavity and a movable diaphragm bounding at least one side of the cavity. In some instances, the adjustable valve is arranged as a boss valve, which includes a portion with a raised, thicker, and/or stiffer bossed area in some instances. The valve system also includes a fluid reservoir in fluid communication with the cavity of the adjustable valve. A first check valve is positioned between the fluid reservoir and the cavity of the adjustable valve along a first fluid passageway. The first check valve prevents fluid flow from the fluid reservoir to the cavity of the adjustable valve. A second check valve is positioned between the fluid reservoir and the cavity of the adjustable valve along a second fluid passageway. The second check valve prevents fluid flow from the cavity of the adjustable valve to the fluid reservoir.

In some instances, the valve system further includes an actuator for controlling a flow of fluid between the fluid reservoir and the cavity of the adjustable valve. In that regard, the actuator is a voltage source and a pair of electrodes in some embodiments. The electrodes are positioned within the fluid reservoir in some instances. In other instances, one of the electrodes is positioned within the fluid reservoir and the other electrode is positioned outside of the fluid reservoir. In one specific instance, the second electrode is positioned within the cavity of the adjustable valve.

In some instances, the fluid reservoir is formed of a material that defines a constant volume cavity during operation. In other instances, the fluid reservoir is formed of a flexible material that defines a variable volume cavity during operation. In some embodiments, an electro-kinetic membrane is positioned between the fluid reservoir and the cavity of the adjustable valve. In such embodiments, an electro-kinetic fluid is received within the fluid reservoir and the cavity of the adjustable valve. In that regard, to control the flow of electro-kinetic fluid one of the electrodes is positioned on opposite sides of the membrane thereby inducing a controllable electro-osmotic pressure gradient. In a different embodiment, the actuator comprises an actuator fluid and a bubble-generating system configured to generate bubbles by converting at least a portion of the actuator fluid to a gas.

In some configurations, the valve system also includes a first adjustable component positioned adjacent the first fluid passageway such that a diaphragm of the first adjustable component is movable between a first position that occupies a first amount of the first fluid passageway and a second position that occupies a second amount of the first fluid passageway, where the second amount is greater than the first amount. Further, in some embodiments, the valve system further includes a second adjustable component positioned adjacent the second fluid passageway such that a diaphragm of the second adjustable component is movable between a first position that occupies a first amount of the second fluid passageway and a second position that occupies a second amount of the second fluid passageway, where the second amount is greater than the first amount. The adjustable components are bubble chambers in some implementations.

In another embodiment consistent with the principles of the present disclosure, a method is provided. The method includes: obtaining pressure readings from a plurality of pressure sensors, determining a desired position of a diaphragm of an adjustable valve based on the obtained pressure readings; actuating an actuator to cause a flow of fluid between a cavity of the adjustable valve and a fluid reservoir to adjust the position of the diaphragm to the desired position; and ceasing actuation of the actuator. In that regard, the diaphragm is maintained in the desired position after actuation of the actuator has ceased. In some instances, the diaphragm is maintained in the desired position after actuation of the actuator has ceased by a pair of opposing check valves positioned between the cavity of the adjustable valve and the fluid reservoir. Further, in some instances, the obtained pressure readings include at least one pressure reading selected from the group consisting of: a pressure within an anterior chamber of an eye, a pressure within a drainage location spaced from the anterior chamber of the eye, and an atmospheric pressure.

It is to be understood that both the foregoing summary and the following detailed description are exemplary and explanatory only and are intended to provide further explanation of the inventions of the present disclosure. Additional advantages, purposes, and alternatives to the specific examples provided will be apparent to one skilled in the art.

BRIEF DESCRIPTION OF THE DRAWINGS

The accompanying drawings, which are incorporated in and constitute a part of this specification, illustrate several embodiments of the present disclosure and together with the description, serve to explain the principles of the present disclosure.

FIG. 13 is a diagrammatic schematic view of the valve system of FIG. 12 showing a diaphragm of the valve system in a first orientation.

FIG. 14 is a diagrammatic schematic view of the valve system of FIG. 12 showing transition of the diaphragm from the first orientation illustrated in FIG. 13 to a second orientation.

FIG. 15 is a diagrammatic schematic view of the valve system of FIG. 12 showing the diaphragm in the second orientation of FIG. 14.

FIG. 16 is a diagrammatic schematic view of the valve system of FIG. 12 showing transition of the diaphragm from the second orientation illustrated in FIG. 15 to a third orientation.

FIG. 17 is a diagrammatic schematic view of the valve system of FIG. 12 showing the diaphragm in the third orientation of FIG. 16.

DETAILED DESCRIPTION OF THE PREFERRED EMBODIMENTS

Figure 1:
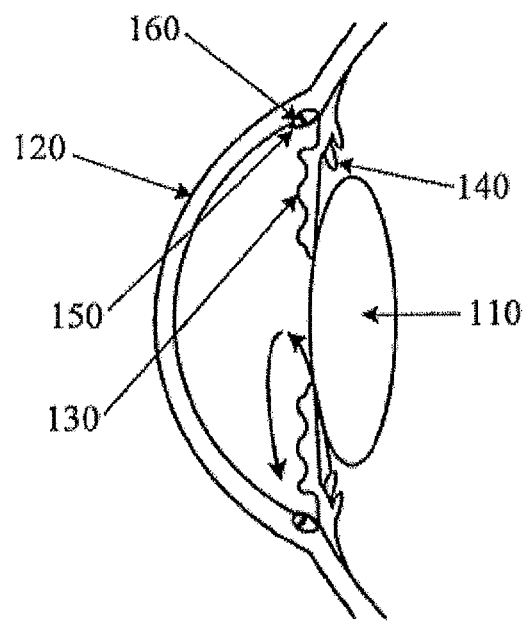
FIG. 1 is a diagram of the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

In some particular instances, embodiments of the present disclosure are configured to be part of the glaucoma drainage devices disclosed in U.S. patent application Ser. No. 12/832,449 filed Jul. 8, 2010, U.S. application Ser. No. 12/685,772 filed Jan. 12, 2010, U.S. application Ser. No. 12/609,043 filed Oct. 30, 2009, and U.S. application Ser. No. 12/563,244 filed Sep. 21, 2009, each of which is hereby incorporated by reference in its entirety for this purpose.

Figure 2:
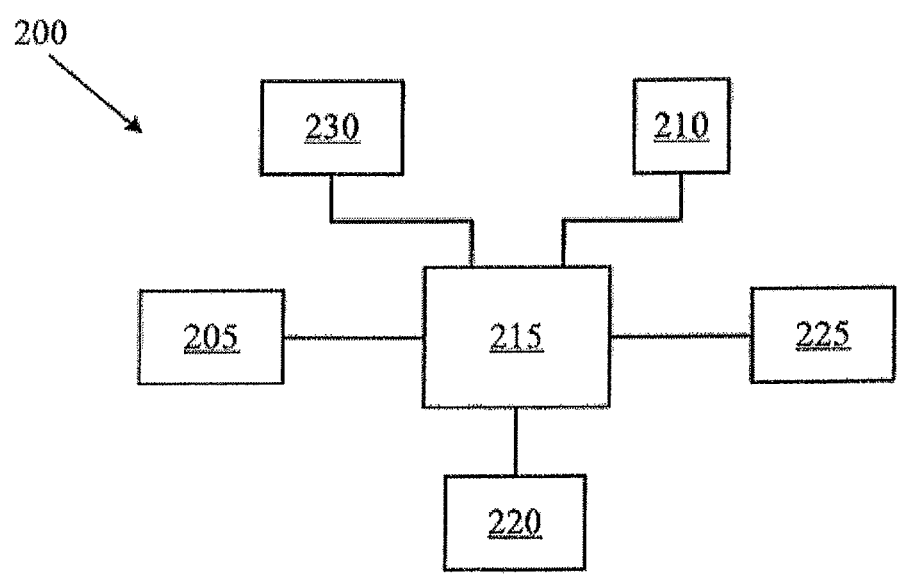
FIG. 2 is a block diagram of an exemplary IOP control system according to one embodiment of the present disclosure.

FIG. 2 is a block diagram of an exemplary IOP control system 200 implantable in an eye of a patient for the treatment of glaucoma or other conditions. The IOP control system 200 is configured in a manner that provides TOP pressure control, but also regulates and controls bleb pressures, reducing complications arising from surgical implant glaucoma treatments. In FIG. 2, the IOP control system 200 includes a power source 205, an IOP sensor system 210, a processor 215, a memory 220, a valve system 230, and a data transmission module 225.

The power source 205 is typically a rechargeable battery, such as a lithium ion or lithium polymer battery, although other types of batteries may be employed. In addition, any other type of power cell is appropriate for power source 205. Power source 205 provides power to the system 200, and more particularly to processor 215. Power source 205 can be recharged via an RFID link or other type of magnetic coupling.

Processor 215 is typically an integrated circuit with power, input, and output pins capable of performing logic functions. In various embodiments, processor 215 is a targeted device controller. In such a case, processor 215 performs specific control functions targeted to a specific device or component, such as a data transmission module 225, power source 205, sensing system 210, valve system 230, or memory 220. In other embodiments, processor 215 is a microprocessor. In such a case, processor 215 is programmable so that it can function to control more than one component of the device. In other cases, processor 215 is not a programmable microprocessor, but instead is a special purpose controller configured to control different components that perform different functions.

Memory 220 is typically a semiconductor memory such as RAM, FRAM, or flash memory. Memory 220 interfaces with processor 215. As such, processor 215 can write to and read from memory 220. For example, processor 215 can be configured to read data from the IOP sensor system 210 and write that data to memory 220. In this manner, a series of IOP readings can be stored in memory 220. Processor 215 is also capable of performing other basic memory functions, such as erasing or overwriting memory 220, detecting when memory 220 is full, and other common functions associated with managing semiconductor memory.

Data transmission module 225 may employ any of a number of different types of data transmission. For example, data transmission module 225 may be an active device such as a radio. Data transmission module 225 may also be a passive device such as the antenna on an RFID tag. In this case, an RFID tag includes memory 220 and data transmission module 225 in the form of an antenna. An RFID reader can then be placed near the system 200 to write data to or read data from memory 220. Since the amount of data typically stored in memory 220 is likely to be small (consisting of IOP readings over a period of time), the speed with which data is transferred is not crucial. Other types of data that can be stored in memory 220 and transmitted by data transmission module 225 include, but are not limited to, power source data (e.g. low battery, battery defect), speaker data (warning tones, voices), IOP sensor data (IOP readings, problem conditions), time stamp data and the like.

Alternatively, data transmission module 225 may be activated to communicate an elevated IOP condition to a secondary device such as a PDA, cell phone, computer, wrist watch, custom device exclusively for this purpose, remote accessible data storage site (e.g. an internet server, email server, text message server), or other electronic device. In one embodiment, a personal electronic device uploads the data to the remote accessible data storage site (e.g. an internet server, email server, text message server). Information may be uploaded to a remote accessible data storage site so that it can be viewed in real time, for example, by medical personnel. For example, in a hospital setting, after a patient has undergone glaucoma surgery and had system 200 implanted, a secondary device may be located next to the patient's hospital bed. Since IOP fluctuations are common after glaucoma surgery (both on the high side and on the low side which is also a dangerous condition), processor 215 can read IOP measurements made by an implanted IOP sensor 210. If processor 215 reads an unsafe IOP condition, data transmission module 225 can alert the patient and medical staff directly or by transmitting the unsafe readings to a secondary device.

Figure 3:
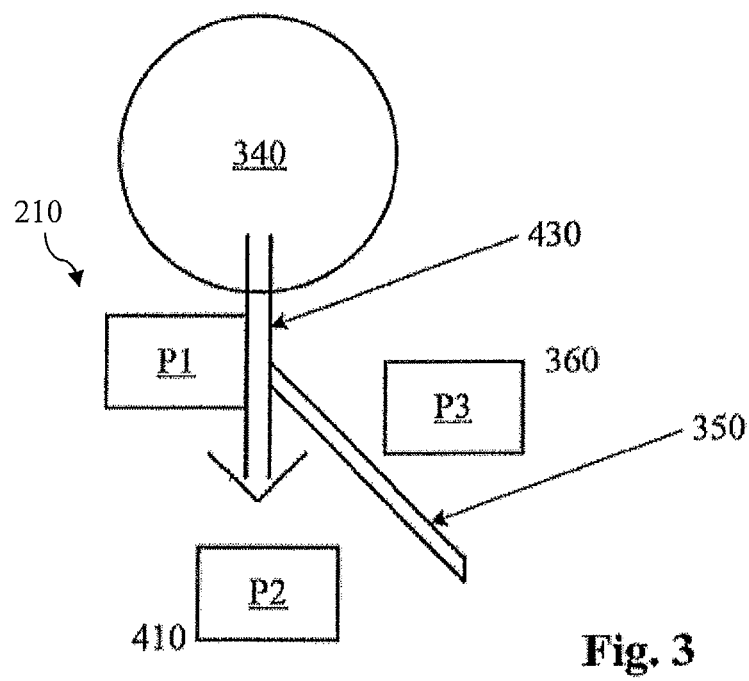
FIG. 3 is a diagram of an TOP sensor system according to one embodiment of the present disclosure.

FIG. 3 is a diagram of the exemplary IOP sensor system 210, the drainage tube 430, valve system 230, and divider 350. In FIG. 3, the exemplary IOP sensor system 210 includes three pressure sensors, P1, P2, and P3. Pressure sensor P1 is located in or is in fluidic communication with the anterior chamber 340, the pressure sensor P2 is located at a drainage site in the subconjunctival space and is arranged to measure bleb pressure, and pressure sensor P3 is located remotely from P1 and P2 in manner to measure atmospheric pressure. In some embodiments, pressure sensor P1 is located in a lumen or tube that is in fluid communication with the anterior chamber.

The drainage tube 430 drains aqueous from the anterior chamber 340 of the eye. The valve system 230 controls the flow of aqueous through the drainage tube 430. In the embodiment shown, the pressure sensor P1 measures the pressure in the tube 430 upstream from the valve system 230 and downstream from the anterior chamber 340. In this manner, pressure sensor P1 measures the pressure in the anterior chamber 340. The expected measurement discrepancy between the true anterior chamber pressure and that measured by P1 when located in a tube downstream of the anterior chamber (even when located between the sclera and the conjunctiva) is very minimal. For example, Poiseuille's law for pipe flow predicts a pressure drop of 0.01 mmHg across a 5-millimeter long tube with a 0.300 millimeter inner diameter for a flow rate of 3 microliters per minute of water.

In some embodiments, the divider 350 separates pressure sensor P2 from pressure sensor P3. Pressure sensor P2 is located at a drainage site (e.g. 410 in FIG. 4). As such, pressure sensor P2 may be located in a pocket, such as a bleb, that generally contains aqueous or in communication with such a pocket, via a tube for example and is in a wet location 410. Pressure sensor P3 is physically separated from pressure sensor P2 by divider 350. Divider 350 is a physical structure that separates the wet location 410 of P2 from the relatively dry (mechanically unstressed) location 360 of P3. In some embodiments, divider 350 is included when the system of the present invention is located on a single substrate. In this configuration, all three pressure sensors (P1, P2, and P3) are located on a substrate that includes tube 430, valve system 230, divider 350, and the other components of the system. Note that the divider 350 may take many forms, such as but not limited to a tube fluidically coupling pressure sensor P3 to a s site away from the substrate or as a pocket residing on the top portion of the substrate away from and fluidically independent of the drainage site.

In some embodiments of the present invention, the atmospheric pressure sensor P3 is located in close proximity to the eye, and in one embodiment, the pressure sensor P3 may be implanted in the eye under the conjunctiva. In such a case, pressure sensor P3 measures a pressure that can be correlated with atmospheric pressure. For example, true atmospheric pressure can be a function of the pressure reading of pressure sensor P3. Pressure sensor P3 may also be located in a dry portion 360 of the subconjunctival space, separate from the drainage location. Regardless of location, pressure sensor P3 is intended to measure atmospheric pressure in the vicinity of the eye or at the eye's surface. One embodiment of the location of P3 is that if the system has the standard Glaucoma Drainage Device (GDD) plate-style shape, then P3 may reside on the top with a barrier preventing it from being crushed while still allowing pressure communication through the conjunctiva and P2 resides on the bottom in direct contact with the drainage site. In a distinctly different embodiment, P3 is not located on the implant but is located outside of the eye as part of a separate external component or subsystem such as a wearable (e.g. glasses, hat, headband) or a device that resides in proximity (e.g. a pillow, nightstand). Such as subsystem, which may or may not include sensor P3, may include the external recharging implant that is at least temporarily placed near the implant location in order to recharge the implant power source 205 and or download data from memory 220 via the data transmission module 225.

Generally, IOP is a gauge pressure reading—the difference between the absolute pressure in the eye (as measured by P1) and atmospheric pressure (as measured by P3). Atmospheric pressure, typically about 760 mm Hg, often varies in magnitude by 10 mmHg or more depending on weather conditions or indoor climate control systems. In addition, the effective atmospheric pressure can vary significantly—in excess of 100 mmHg—if a patient goes swimming, hiking, riding in an airplane, etc. Such a variation in atmospheric pressure is significant since IOP is typically in the range of about 15 mm Hg. Thus, for accurate monitoring of IOP, it is desirable to have pressure readings for the anterior chamber (as measured by P1) and atmospheric pressure in the vicinity of the eye (as measured by sensor P3).

Therefore, in one embodiment of the present invention, pressure readings are taken by P1 and P3 simultaneously or nearly simultaneously over time so that the actual IOP can be calculated (as P1−P3 or P1−f(P3)), where f(P3) indicates a function of P3. The pressure readings of P1 and P3 can be stored in memory 220 by processor 215. They can later be read from memory so that actual IOP over time can be interpreted by a physician.

Pressure sensors P1, P2, and P3 can be any type of pressure sensors suitable for implantation in the eye. They each may be the same type of pressure sensor, or they may be different types of pressure sensors. For example, pressure sensors P1 and P2 may be the same type of pressure sensor (implanted in the eye), and pressure sensor P3 may be a different type of pressure sensors (in the vicinity of the eye).

Figure 4:
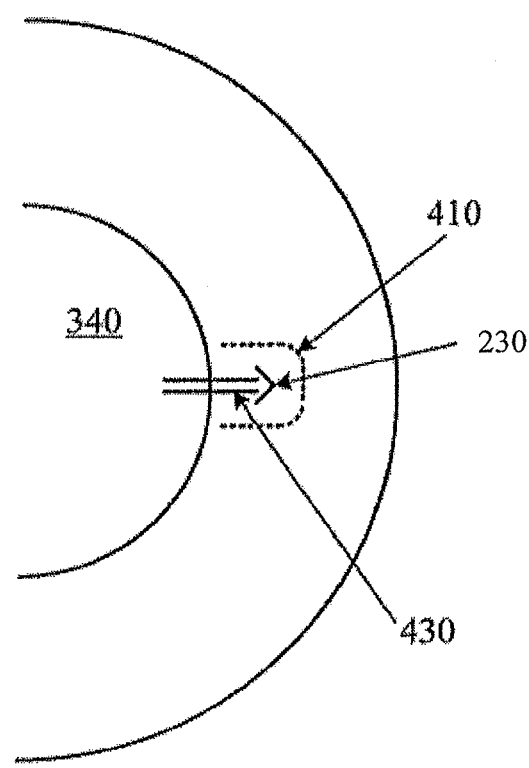
FIG. 4 is a diagram of a drainage device incorporating an IOP sensor system according to one embodiment of the present disclosure.

In another embodiment of the present invention, pressure readings taken by pressure sensors P1 and P2 can be used to control a device that drains aqueous from the anterior chamber 340. FIG. 4 is a diagram of one possible application of the sensors in a system utilizing the readings of pressures sensors P1-P3. In FIG. 4, pressure sensor P1 measures the pressure in the anterior chamber 340 of the eye. Pressure sensor P2 measures the pressure at a drainage site 410.

The drainage tube 430 may be arranged to shunt fluid from the anterior chamber 340 to the drainage location 410, which may be any of numerous locations within the eye. For example, some tubes are arranged to shunt aqueous from the anterior chamber 340 to the subconjunctival space thus forming a bleb under the conjunctiva or alternatively, to the subscleral space thus forming a bleb under the sclera. Other tube designs shunt aqueous from the anterior chamber to the suprachoroidal space, the supraciliary space, the juxta-uveal space, or to the choroid, forming blebs in those respective locations. In other applications, the drainage tube shunts aqueous from the anterior chamber to Schlemm's canal, a collector channel in Schlemm's canal, or any of a number of different blood vessels like an episcleral vein. In some examples, the drainage tube even shunts aqueous from the anterior chamber to outside the conjunctiva. Each of these different anatomical locations to which aqueous is shunted is an example of a drainage location 410. Other examples of a drainage location 410 include, but are not limited to: a subconjunctival space, a suprachoroidal space, a subscleral space, a supraciliary space, Schlemm's canal, a collector channel, an episcleral vein, and a uveo-scleral pathway.

In FIG. 4, the tube 430 with the valve system 230 on one end is located with one end in the anterior chamber 340 and the other end in the drainage location 410, with P1 located within the anterior chamber 340. The valve system 230 controls the flow of aqueous from the anterior chamber 340 to drainage location 410. As indicated above, the pressure sensor P1 is located in the anterior chamber (as illustrated in FIG. 4) or located in the subconjunctival space in fluid communication with the anterior chamber 340 (as illustrated in FIG. 3), in either version pressure sensor P1 is located upstream from valve system 230.

Since pressure sensor P1 measures the pressure in the anterior chamber 340 and pressure sensor P2 measures pressure at the drainage location 410, the difference between the readings taken by these two pressure sensors (P1−P2) provides an indication of the pressure differential between the anterior chamber 340 and the drainage location 410. In one embodiment, this pressure differential dictates the rate of aqueous flow from the anterior chamber 340 to the drainage location 410.

One complication involved with surgery that shunts the anterior chamber 340 to a drainage location 410 is hypotony—a dangerous drop in IOP that can result in severe consequences. It is desirable to control the rate of aqueous outflow from the anterior chamber 340 to the drainage location 410 so as to prevent hypotony. Readings from pressure sensors P1, P2, and P3 can be used to control the flow rate through tube 430 by controlling the valve system 230. For example, the valve system 230 can be controlled based on the pressure readings from pressure sensors P1, P2, and P3.

In another embodiment of the present invention, IOP (based on readings from pressure sensor P1 and pressure sensor P3) can be controlled by controlling valve system 230. In this manner, IOP is the control parameter. To accomplish this, the valve system 230 can be adjusted to maintain a particular IOP (like an IOP of 15 mm Hg). Valve system 230 may be opened more at night than during the day to maintain a particular IOP. In other embodiments, an IOP drop can be controlled. Immediately after surgery, IOP can drop precipitously. Valve system 230 can be adjusted to permit a gradual drop in IOP based on readings from pressure sensors P1 and P3. Note that the physician would be able to set the high/low IOP thresholds wirelessly to meet each patient's specific requirements.

In another embodiment of the present invention, readings from pressure sensor P2 (or from the difference between pressure sensor P2 and atmospheric pressure as measured by P3) can be used to control valve system 230 so as to control the morphology of a bleb. One of the problems associated with implant surgery is bleb failure. A bleb can fail due to poor formation or fibrosis. The pressure in the bleb is one factor that determines bleb morphology. As explained above, too much pressure can cause a bleb to migrate to an undesirable location or can lead to fibrosis. The pressure of the bleb can be controlled by using the reading from pressure sensor P2 (at drainage location 410—in this case, a bleb). In one embodiment of the present invention, the difference between the pressure in the bleb (as measured by P2) and atmospheric pressure (as measured by P3) can be used to control valve system 230 to maintain a desired bleb pressure. In this manner, the pressure sensors used to determine IOP as defined in the present invention can also be used to properly maintain a bleb.

Valve system 230 may be controlled by microprocessor 215 based on input data received from the sensors. A desired pressure differential (that corresponds to a desired flow rate) can be maintained by controlling the operation of valve system 230. Likewise, a desired IOP, IOP change rate, or bleb pressure can be controlled by controlling the operation of valve system 230. Furthermore, flow across the valve may drastically vary with time.

Finally, there are many other similar uses for the IOP sensor system 210. For example, various pressure readings can be used to determine if tube 430 is occluded or obstructed in some undesirable manner. As such, failure of a drainage device can be detected. Further, the pressure sensors have configurations other than those illustrated that are utilized in some embodiments (e.g., end cap implementations, incorporation into a portion of a valve system, etc.). In that regard, the IOP sensor configurations disclosed in U.S. patent application Ser. No. 12/832,449 filed Jul. 8, 2010, U.S. application Ser. No. 12/685,772 filed Jan. 12, 2010, U.S. application Ser. No. 12/609,043 filed Oct. 30, 2009, and U.S. application Ser.

No. 12/563,244 filed Sep. 21, 2009, each of which is hereby incorporated by reference in its entirety for this purpose, are utilized in some instances. In that regard, readings from the IOP sensor configurations are utilized to control the valve systems of the present disclosure in some embodiments.

Figure 5:
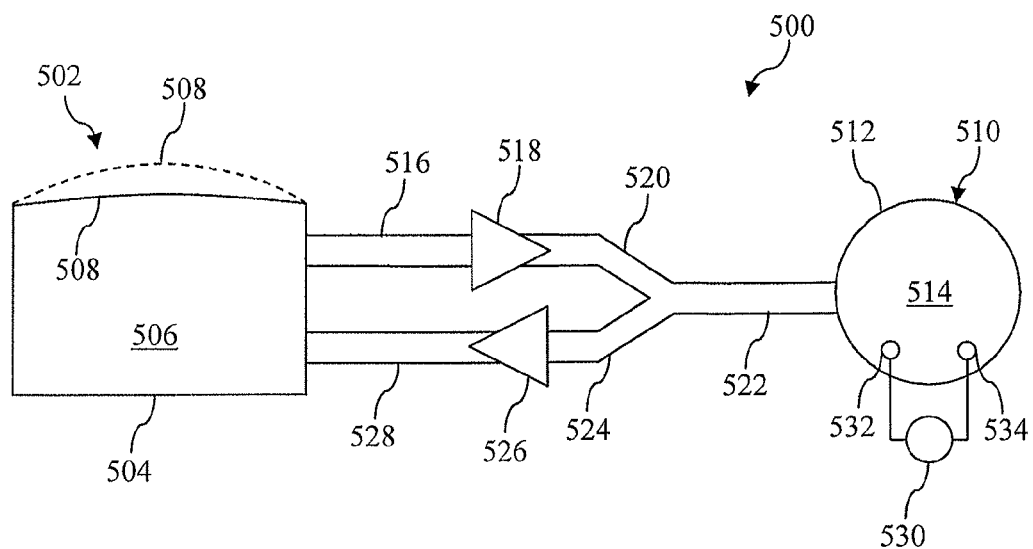
FIG. 5 is a diagrammatic schematic view of a valve system according to one embodiment of the present disclosure.

Referring now to FIG. 5, shown therein is a diagrammatic schematic view of a valve system 500 according to one embodiment of the present disclosure. As shown, the valve system 500 includes an adjustable valve 502. The adjustable valve 502 is comprised of a housing 504 that defines a cavity 506 that contains a fluid. A membrane or diaphragm 508 is coupled to the housing 504 such that the diaphragm defines an upper boundary of the cavity 506. In that regard, the diaphragm 508 is formed of a material that is more flexible than the material forming the housing 504 such that the diaphragm 508 is movable between different positions based upon the amount of fluid and/or pressure within the cavity 506. In some instances, the diaphragm 508 is formed of silicone rubber, polyimide, a thin silicon membrane, Parylene, a thin silicon nitride membrane, gold, Parylene/gold/Parylene composite membranes and the like and/or other suitable materials. As the amount of fluid within the cavity 506 is increased, the pressure within the cavity increases, which results in the displacement of the diaphragm 508 away from the cavity (upwards as viewed in FIG. 5). An exemplary displaced position of the diaphragm 508 corresponding to an increased amount of fluid and pressure within cavity 506 is illustrated in phantom in FIG. 5. In some instances, the adjustable valve 502 is implemented as a boss valve (e.g., similar to the boss valve illustrated in FIGS. 18-20 and described below).

In order to control the amount of fluid within the cavity 506 and, thereby, the relative position of the diaphragm 508, the adjustable valve 502 is in communication with a fluid reservoir 510. The fluid reservoir 510 includes a housing 512 that defines a cavity 514 that also contains fluid. In the present embodiment, the housing 512 is formed of a relatively rigid material, such as glass, polymer (e.g. polycarbonate), silicon, silicon dioxide, metal such as titanium, etc. In that regard, the housing 512 is designed to maintain its shape in the current embodiment. Accordingly, the housing 512 defines a constant volume for cavity 514 during use.

The cavity 506 of the adjustable valve 502 is in fluid communication with the cavity 514 of the fluid reservoir 510. This allows a flow of fluid between the cavities 506 and 514 such that a desired amount of fluid is held within cavity 506 in order to maintain the diaphragm 508 in a desired position. In that regard, a lumen 516 extends from cavity 506 to a check valve 518. Check valve 518 allows fluid flow only in the direction away from cavity 506 and towards cavity 514. That is, check valve 518 prevents fluid flow from cavity 514 towards cavity 506. A lumen 520 connects lumen 516 and check valve 518 to a lumen 522 that extends from cavity 514. In that regard, in the illustrated embodiment lumen 522 serves as both an egress and ingress lumen for cavity 514, as discussed below. In other embodiments, two separate lumens are provided, one for egress of fluid from cavity 514 and one for ingress of fluid to cavity 514.

In the illustrated embodiment, in addition to being in fluid communication with lumen 520, lumen 522 is also in fluid communication with lumen 524. Lumen 524, in turn, extends to a check valve 526. Check valve 526 allows fluid flow only in the direction away from cavity 514 and towards cavity 506. That is, check valve 526 prevents fluid flow from cavity 506 towards cavity 514. A lumen 528 connects lumen 524 and check valve 526 to cavity 506. Generally, the check valves 518, 526 can have any desired cracking pressure. In some instances, check valve 526 has a cracking pressure near zero (for example, 0.1 mmHg or lower) and check valve 518 has a cracking pressure approximately equal to the pressure required to maintain membrane 508 in the maximum outward position meaning valve 502 is fully closed. For example, such a pressure might be 100 mmHg with a tolerance of about 5 mmHg. In such an embodiment, the cavity 514 operates as an electrolysis bubble chamber (see below). Actuation of electrodes 532 and 534 cause bubbles to form in the fluid within cavity 514 thereby causing pressure to increase and liquid to flow through lumens 522 and 524, check valve 526, lumen 528 and into cavity 506. This causes pressure in cavity 506 to increase thereby expanding membrane 508 of valve 502. Once membrane 508 is set to a desired location, the pressure in cavity 506 is approximately equal to the pressure of cavity 514. The pressure in cavity 514 then decays either naturally or by intent (i.e. via reversing electrical operation of voltage source 530); however, pressure in cavity 506 is temporarily maintained by check valve 518—until pressure difference is greater than that of the cracking pressure of check valve 518. Once pressure difference across check valve 518 is greater than its cracking pressure, flow is initiated from cavity 506 to cavity 514 and membrane 508 is lowered; that is, valve 502 becomes more open. In such an embodiment, the lowest setting of membrane 508 occurs at some intermediate pressure between zero and the maximum design pressure (e.g. 100 mmHg), for example, approximately half (50 mmHg). The non-zero pressure is realized since the non-zero check valve requires that some of the working fluid remain in cavity 506. The design then of valve 502 is such that the membrane 508's location—relative to the channel in which it lies—produces the maximum open design pathway when the minimum (though non-zero) pressure is achieved in cavity 506. As the function of the check valves is to ensure that fluid flows in a particular direction or pressure gradient, any type of check valve or one way valve may be used, including, for example, a flapper or Reed valve.

The valve system 500 also includes a voltage source 530 that is in electrical communication with the fluid within cavity 514. More specifically, a pair of electrodes 532 and 534 that are connected to the voltage source 530 are positioned in electrical communication with the fluid within cavity 514. The electrodes 532, 534 are formed of a conductive material, such as platinum, gold, copper, silver, silver-chloride, and/or other conductive materials. Voltage for gas generation via electrolysis of water is typically about 1.2 V for Platinum electrodes. Electrical currents are in the order of fractions of micro amps to several micro amps. The faster the actuation desired, the higher the current level that can be chosen. The higher the cell's overall electrical resistance, including through the electrolyte, the higher the power that will be required for a given performance level (measured by parameters such as pressure vs time for instance).

In use, a voltage is applied across electrodes 532, 534 in order to cause the formation of bubbles within cavity 514. In some instances, the bubbles are formed through electrolysis. In that regard, the fluid utilized within the valve system 500 is an electrolysis solution, which is typically water with a small electrolytic additive such as a salt and/or one or more of the following: $KNO_3$, $H_2SO_4$, $CaSO_4$, $MgSO_4$, $CaCO_3$, $K_2SO_4$, $Na_2SO_4$, $LiSO_4$, $NaOH$, $KOH$, $H_2NO_4$, and $CuSO_4$. If salt additive is used, the solution could be Balanced Salt Solution (BSS) which is commonly introduced into the eye during ophthalmic surgery (though possibly unwanted gases may be generated during the process). The electrodes 532, 534 apply voltage to the volume of water or saline solution within the cavity 514 to cause the electrolysis. As is known, electrical current applied through water (via a voltage applied across one or more pair of electrodes) results in the breaking of the molecular bonds of the water to produce hydrogen and oxygen gases. Since the volume of the resulting gases is much greater than the corresponding volume of the water that produces the gases and the housing 512 defines a constant volume for cavity 514, the pressure within cavity 514 is increased by the creation of the gases. With the increased pressure, fluid will be forced out of cavity 514 towards cavity 506. As the amount of fluid within cavity 506 is increased, the diaphragm 508 will be displaced upward, as viewed in FIG. 5.

As the gases within cavity 514 recombine (i.e., return to a liquid state with a reduced volume) the pressure within cavity 514 will decrease. When the pressure within cavity 514 becomes less than the pressure within cavity 506, fluid will flow from cavity 506 towards cavity 514. As the amount of fluid within cavity 506 is decreased, the diaphragm 508 will be displaced downward, as viewed in FIG. 5. In some instances, reversing the voltage applied by the electrodes 532, 534 speeds up the recombination process. Accordingly, in some instances the pressure within cavity 514 can be controlled by regulating the voltage applied to the electrodes 532, 534 in order to vary the positioning of diaphragm 508. In that regard, by controlling the pressure within cavity 514, the flow of fluid between cavity 514 and cavity 506 is likewise controlled. In that regard, in some instances a processor in communication with an IOP sensor configuration is utilized to determine an appropriate position for the diaphragm 508 and the corresponding voltage, if any, that should be applied by the voltage source 530 to cause the appropriate flow of fluid between the cavities 506, 514 to achieve the desired diaphragm position. It is understood that processor and IOP sensor based control may be utilized to control the positions of valve(s)/diaphragm(s) with each of the systems of the present disclosure, even if such control is not explicitly mentioned with respect to a particular system.

The arrangement of valve system 500 has significant advantages over a direct bubble-actuation system (e.g., where electrolysis or thermal bubble generation is performed directly within the cavity 506). For example, the check valves 518, 526 help to maintain a constant pressure within the cavity 506 and a corresponding fixed position of diaphragm 508 for longer periods of time. In that regard, in a direct bubble-actuation arrangement the pressure is constantly changing (e.g., decreasing during recombination), which results in a corresponding constant change in the diaphragm position. It is understood that while the operation of valve system 500 has been described in terms of electrolysis, other types of chemical reactions, thermal nucleation, and/or mechanical arrangements (like a piston or other moving part) may be used to change the pressure and/or volume of cavity 514 to achieve similar functionality.

Figure 12:
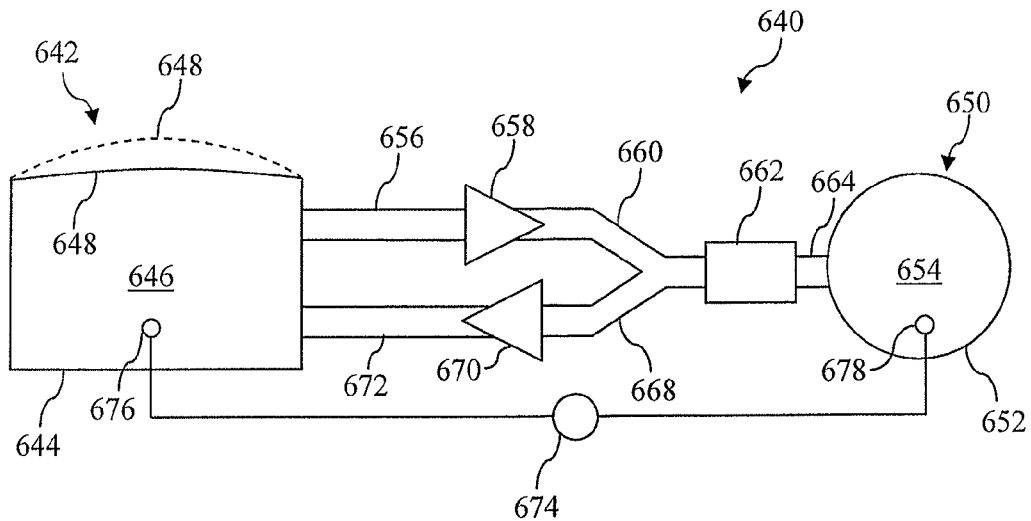
FIG. 12 is a diagrammatic schematic view of a valve system according to another embodiment of the present disclosure.

In an alternative embodiment, one of the electrodes 532 or 534 is positioned in electrical communication with cavity 514, while the other electrode 532 or 534 is positioned in electrical communication with cavity 506 (See, for example, FIG. 12 for a similar arrangement of electrodes). By separating the two electrodes between the two cavities 506 and 514, recombination of the bubbles to once again form liquid water is slowed because of the spatially separated generation of $H_2$ and $O_2$.

Figure 26:
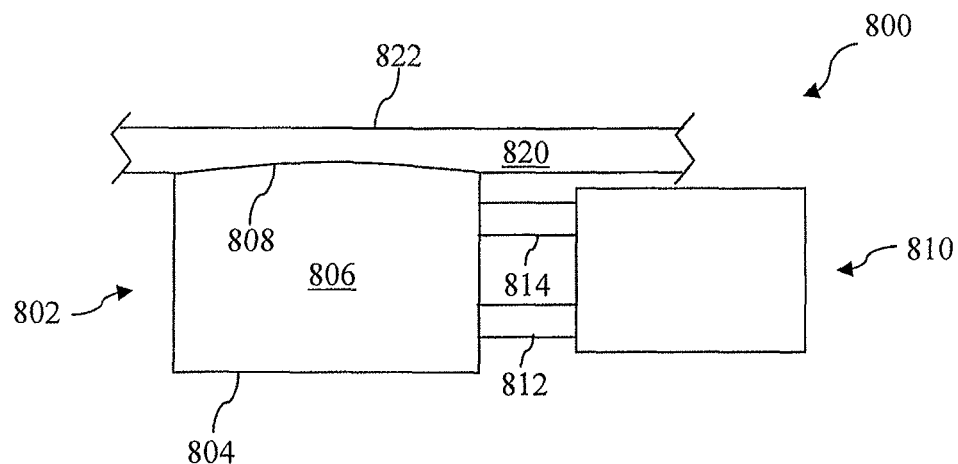
FIG. 26 is a diagrammatic schematic view of a valve system of the present disclosure interfacing with a lumen, where a diaphragm of the valve system is shown in a first orientation with respect to the lumen.
Figure 27:
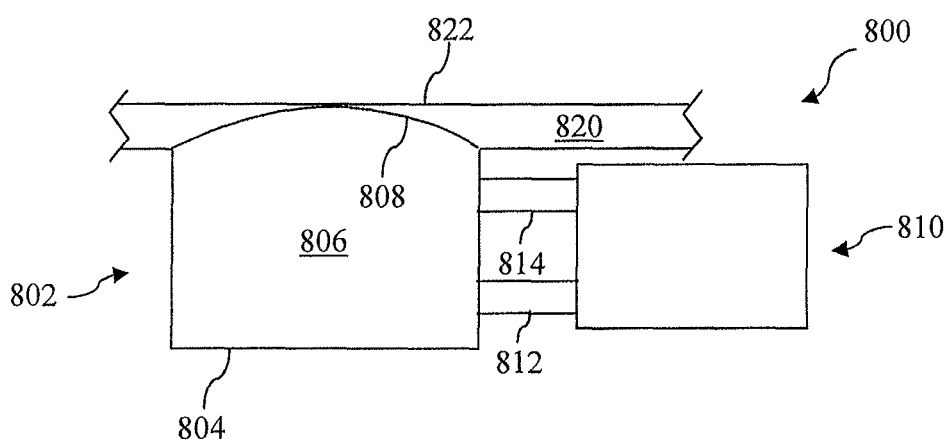
FIG. 27 is a diagrammatic schematic view of a valve system of the present disclosure interfacing with a lumen similar to FIG. 26, but showing the diaphragm of the valve system in a second orientation with respect to the lumen.

In some instances, the valve system 500 is selectively moved between positions that obstruct fluid flow through an adjacent lumen (see, for example, FIGS. 26 and 27). The ability of the diaphragm 508 to be displaced allows for a variable level of flow restriction through the lumen by the varying how far into the lumen the diaphragm goes. In some instances, the diaphragm 508 is movable between a position that does not block the lumen at all (0% blockage), a position that blocks the lumen completely (100% blockage), and positions therebetween that partially block the lumen (0.01-99.9% blockage). The particular range of lumen blockages provided by the valve system 500 can be selected for particular uses and may include any subset of lumen blockages between 0% and 100% blockage. In one use, the valve system 500 controls the amount of aqueous that enters the drainage location and exits the anterior chamber of the eye. In some instances, the valve system 500 controls the aqueous flow based on readings from pressure sensor(s), such as P1, P2, and P3, as described above.

Controlling aqueous flow can reduce the chances of hypotony after filtration surgery, maintain a suitable IOP, and/or control the amount of stagnant aqueous in the drainage location. When the drainage location is a subconjunctival bleb, controlling the amount of stagnant aqueous in the bleb can help maintain proper bleb morphology and reduce the amount of fibrosis. Too much stagnant aqueous in a bleb can lead to fibrosis. It has been postulated that fibroblasts form in stagnant aqueous and that too much tension on the bleb wall (i.e., too high a pressure in the bleb) can lead to bleb failure. Accordingly, the use of valves and valve systems of the present disclosure, including valve system 500, can lead to proper bleb maintenance, which decreases the chances of these deleterious side effects. In some instances, the diaphragm 508 is repeatedly transitioned between an open position and a closed position to cause a flow of fluid through an associated lumen (i.e., the diaphragm is utilized to pump fluid). In this manner, the valves and valve systems of the present disclosure can be utilized as a pump system.

Figure 6:
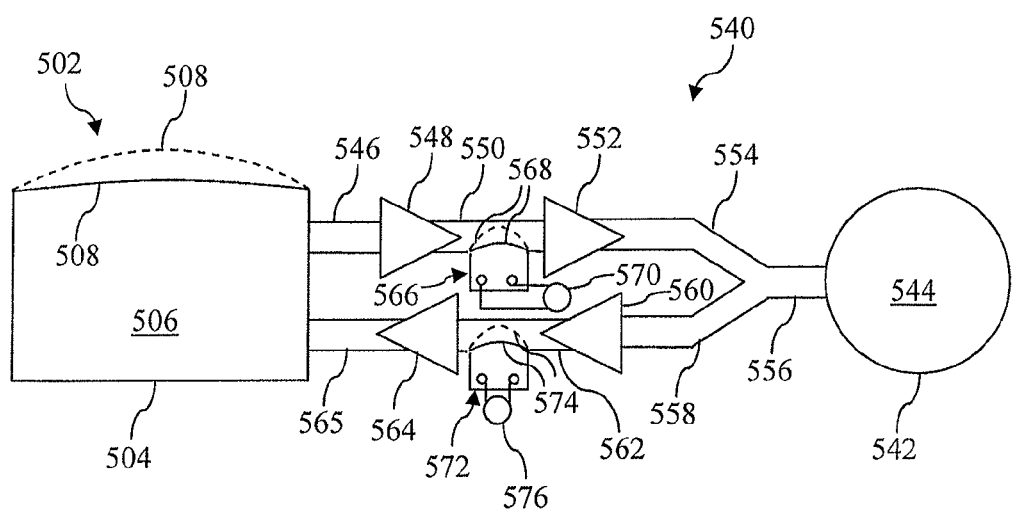
FIG. 6 is a diagrammatic schematic view of a valve system according to another embodiment of the present disclosure.

Referring now to FIG. 6, shown therein is a diagrammatic schematic view of a valve system 540 according to another embodiment of the present disclosure. As shown, the valve system 540 includes an adjustable valve 502 similar to that of valve system 500. The adjustable valve 502 is comprised of a housing 504 that defines a cavity 506 that contains fluid. A membrane or diaphragm 508 is coupled to the housing 504 such that the diaphragm defines an upper boundary of the cavity 506. In that regard, the diaphragm 508 is formed of a material that is more flexible than the material forming the housing 504 such that the diaphragm 508 is movable between different positions based upon the amount of fluid and/or pressure within the cavity 506. As the amount of fluid within the cavity 506 is increased, the pressure within the cavity increases, which results in the displacement of the diaphragm 508 away from the cavity (upwards as viewed in FIG. 6). An exemplary displaced position of the diaphragm 508 corresponding to an increased amount of fluid and pressure within cavity 506 is illustrated in phantom.

In order to control the amount of fluid within the cavity 506 and, thereby, the relative position of the diaphragm 508, the adjustable valve 502 is in communication with a fluid reservoir 542. The fluid reservoir 542 includes a housing that defines a cavity 544 that also contains fluid. In the present embodiment, the housing of the fluid reservoir 542 is formed of a relatively flexible material, such as Parylene, silicone rubber, thin silicon membranes, Parylene/Au/Parylene composites, polyimide, thin silicon nitride membranes, gold membranes and the like. In some instances, the housing is an expandable pouch or bag. In that regard, the housing of fluid reservoir 542 is designed to inflate and deflate depending on the amount of fluid received within cavity 544. Accordingly, the housing defines a varying volume for cavity 544 during use.

The cavity 506 of the adjustable valve 502 is in fluid communication with the cavity 544 of the fluid reservoir 542. This allows a flow of fluid between the cavities 506 and 544 such that a desired amount of fluid is held within cavity 506 in order to maintain the diaphragm 508 in a desired position. In that regard, a fluid channel 546 extends from cavity 506 to a check valve 548. Check valve 548 allows fluid flow only in the direction away from cavity 506 and towards cavity 544. That is, check valve 548 prevents fluid flow from cavity 544 towards cavity 506. A fluid channel 550 connects fluid channel 546 and check valve 548 to another check valve 552. Similar to check valve 548, check valve 552 allows fluid flow only in the direction away from cavity 506 and towards cavity 544. A fluid channel 554 connects check valve 552 to a fluid channel 556 that extends from cavity 544. In that regard, in the illustrated embodiment, fluid channel 556 serves as both an egress and ingress fluid channel for cavity 544. In other embodiments, two separate fluid channels are provided, one for egress of fluid from cavity 544 and one for ingress of fluid to cavity 544.

In the illustrated embodiment, in addition to being in fluid communication with fluid channel 554, fluid channel 556 is also in fluid communication with fluid channel 558. Fluid channel 558, in turn, extends to a check valve 560. Check valve 560 allows fluid flow only in the direction away from cavity 544 and towards cavity 506. That is, check valve 560 prevents fluid flow from cavity 506 towards cavity 544. A fluid channel 562 connects fluid channel 558 and check valve 560 to another check valve 564. Similar to check valve 560, check valve 564 allows fluid flow only in the direction away from cavity 544 and towards cavity 506. A fluid channel 565 connects check valve 564 to cavity 506. Generally, the check valves 548, 552, 560, and 564 can have any desired cracking pressure. As the function of the check valves is to ensure that fluid flows in a particular, any type of check valve or one way valve may be used, including, for example, a flapper or Reed valve.

The valve system 540 also includes a bubble chamber 566 that is in communication with fluid channel 550. More specifically, a flexible membrane or diaphragm 568 of the bubble chamber is in communication with the fluid channel 550. In that regard, the diaphragm 568 can be selectively moved between positions that occupy varying amounts of the volume of the fluid channel. In some instances, the diaphragm 568 is movable between a position that does not occupy the fluid channel at all (0% occupation), a position that occupies the entire fluid channel completely (100% occupation), and positions therebetween that partially occupy the fluid channel (0.01-99.9% occupation). The particular range of fluid channel occupations provided by the diaphragm can be selected for particular uses and may include any subset of fluid channel occupations between 0% and 100% occupation. Two exemplary positions of the diaphragm 568 are shown in FIG. 6 (an increased occupation position is shown in phantom).

A voltage source 570 is in electrical communication with a fluid within the bubble chamber 566. More specifically, electrodes coupled to the voltage source 570 are positioned in electrical communication with the fluid within bubble chamber. In use, a voltage is applied across the electrodes in order to cause the formation of bubbles within the bubble chamber 566. In some instances, the bubbles are formed through electrolysis. In that regard, the fluid received within the bubble chamber 572 is an electrolysis solution, which is typically water with a small electrolytic additive such as a salt and/or one or more of the following: KNO3, H2SO4, CaSO4, MgSO4, CaCO3, K2SO4, Na2SO4, LiSO4, NaOH, KOH, H2NO4, and CuSO4. If salt additive is used, the solution could be Balanced Salt Solution (BSS) which is commonly introduced into the eye during ophthalmic surgery (though note the potential unwanted gases associated with electrolysis of BSS, as mentioned previously). The electrodes apply a voltage to the volume of fluid within the bubble chamber 566 to cause electrolysis. As is known, electrical current applied through water (via a voltage applied across one or more pair of electrodes) results in the breaking of the molecular bonds of the water to produce hydrogen and oxygen gases. Since the volume of the resulting gases is greater than the corresponding volume of the water that produces the gases, the diaphragm 568 will be displaced upward, as viewed in FIG. 6. As the diaphragm 568 is displaced upward it will occupy a greater amount of the volume of the fluid channel 550, which will force the fluid within fluid channel 550 towards cavity 544. In that regard, check valves 548 and 552 ensure that fluid flows only the direction away from cavity 506 and towards cavity 544 as the diaphragm 568 increases the amount of occupation of fluid channel 550.

As the gases within bubble chamber 566 recombine (i.e., return to a liquid state with a reduced volume) the diaphragm will be displaced downward, as viewed in FIG. 6. In some instances, reversing the voltage applied by the electrodes of the voltage source 570 speeds up the recombination process. As the diaphragm is displaced downward it will occupy a lesser amount of the volume of the fluid channel 550, which will create a negative gauge pressure within fluid channel 550 causing fluid to flow from cavity 506 through check valve 548 and into fluid channel 550 towards cavity 544. Accordingly, in some instances the displacement of the diaphragm 568 of the bubble chamber 566 is controlled by regulating the voltage applied to the electrodes of the voltage supply 570. In that regard, by controlling the electrolysis process within the bubble chamber 566, the flow of fluid from cavity 506 to cavity 544 is likewise controlled. While the operation of bubble chamber 566 has been described in terms of electrolysis, other types of chemical reactions, thermal nucleation, and/or mechanical arrangements (like a piston or other moving part) may be used to change the position of diaphragm 568.

In one embodiment, check valves 548 and 552 and bubble chamber 566 together function as a one way pumping system, forcing fluid on command to flow from cavity 506 to cavity 544. In order to maintain pressure in cavity 506 when desired, check valve 548 has a non-zero cracking pressure approximately equal to the pressure required to maintain membrane 568 in the maximum outward position meaning valve 502 is fully closed. For example, such a pressure might be 100 mmHg with a tolerance of about 5 mmHg. In this instance, check valve 552 has a cracking pressure near zero (for example, 0.1 mmHg or lower). In this way, if the pressure in 506 is to be reduced (diaphragm 508 lowered), then activation voltage supply 570 creates bubbles and thus pressure inside bubble chamber 566 increases, which causes diaphragm 568 to rise. This event forces fluid from fluid channel 550 through check valve 552. The relaxation (natural or forced) of bubble chamber 566 and diaphragm 568 will then cause fluid to exit cavity 506 and flow through check valve 548 into fluid channel 550. Conversely, if it is desired to raise diaphragm 508, then bubble chamber 568 is not activated but rather fluid is forced into cavity 506 from cavity 544 via fluid channel 558. This occurs by the pump-like operation of check valves 564 and 562 and bubble chamber 572 (see below for details regarding these components). In such a case, check valves 560 and 564 have a cracking pressure near zero (for example, 0.1 mmHg or lower). Net flow from cavity 544 to cavity 506 is realized by the repetitive expansion and contraction of diaphragm 574. That is, when voltage supply 576 is activated in such that bubbles are generated in bubble chamber 572, then pressure causes diaphragm 574 to expand and thus forces fluid from fluid channel 562 to fluid channel 565 (and into cavity 506) through check valve 564. The relaxation (natural or forced) of bubble chamber 572 and diaphragm 574 will then cause fluid to exit cavity 544 and flow through check valve 560 into fluid channel 562.

The valve system 540 also includes a bubble chamber 572 that is in communication with fluid channel 562. More specifically, a flexible membrane or diaphragm 574 of the bubble chamber is in communication with the fluid channel 562. In that regard, the diaphragm 574 can be selectively moved between positions that occupy varying amounts of the volume of the fluid channel. In some instances, the diaphragm 574 is movable between a position that does not occupy the fluid channel at all (0% occupation), a position that occupies the entire fluid channel completely (100% occupation), and positions therebetween that partially occupy the fluid channel (0.01-99.9% occupation). The particular range of fluid channel occupations provided by the diaphragm 574 can be selected for particular uses and may include any subset of fluid channel occupations between 0% and 100% occupation. Two exemplary positions of the diaphragm 574 are shown in FIG. 6 (an increased occupation position is shown in phantom).

A voltage source 576 is in electrical communication with a fluid within the bubble chamber 572. More specifically electrodes coupled to the voltage source 576 are positioned in electrical communication with the fluid within bubble chamber. In use, a voltage is applied across the electrodes in order to cause the formation of bubbles within the bubble chamber 572. In some instances, the bubbles are formed through electrolysis. In that regard, the fluid received within the bubble chamber 572 is an electrolysis solution, which is typically water with a small electrolytic additive such as a salt and/or one or more of the following: KNO3, H2SO4, CaSO4, MgSO4, CaCO3, K2SO4, Na2SO4, LiSO4, NaOH, KOH, H2NO4, and CuSO4. If salt additive is used, the solution could be Balanced Salt Solution (BSS) which is commonly introduced into the eye during ophthalmic surgery (though note the potential unwanted gases associated with electrolysis of BSS, as mentioned previously). The fluid within bubble chamber 572 may be the same or different than the fluid received within bubble chamber 566.

The electrodes of voltage source 576 apply a voltage to the volume of fluid within the bubble chamber 572 to cause electrolysis. As is known, electrical current applied through water (via a voltage applied across one or more pair of electrodes) results in the breaking of the molecular bonds of the water to produce hydrogen and oxygen gases. Since the volume of the resulting gases is greater than the corresponding volume of the water that produces the gases, the diaphragm 574 will be displaced upward, as viewed in FIG. 6. As the diaphragm 574 is displaced upward it will occupy a greater amount of the volume of the fluid channel 562, which will force the fluid within fluid channel 562 towards cavity 506. In that regard, check valves 560 and 564 ensure that fluid flows only the direction away from cavity 544 and towards cavity 506 as the diaphragm 574 increases the amount of occupation of fluid channel 562.

As the gases within bubble chamber 572 recombine (i.e., return to a liquid state with a reduced volume) the diaphragm will be displaced downward, as viewed in FIG. 6. In some instances, reversing the voltage applied by the electrodes of the voltage source 576 speeds up the recombination process. As the diaphragm is displaced downward it will occupy a lesser amount of the volume of the fluid channel 562, which will create a negative gauge pressure within fluid channel 562 causing fluid to flow from cavity 544 through check valve 560 and into fluid channel 562 towards cavity 506. Accordingly, in some instances the displacement of the diaphragm 574 of the bubble chamber 572 is controlled by regulating the voltage applied to the electrodes of the voltage supply 576. In that regard, by controlling the electrolysis process within the bubble chamber 572, the flow of fluid from cavity 544 to cavity 506 is likewise controlled. While the operation of bubble chamber 572 has been described in terms of electrolysis, other types of chemical reactions, thermal nucleation, and/or mechanical arrangements (like a piston or other moving part) may be used to change the position of diaphragm 574.

By coordinating control of the bubble chambers 566 and 572, the valve system 540 can be utilized to selectively move the diaphragm 508 of valve 502 between positions that obstruct fluid flow through an adjacent lumen or fluid channel (See, for example, FIGS. 26 and 27) in varying amounts. As discussed above with respect to valve system 500, the ability of the diaphragm 508 to be displaced allows for a variable level of flow restriction and/or pumping through the lumen or fluid channel by the varying how far into the lumen or fluid channel the diaphragm goes.

Figure 7:
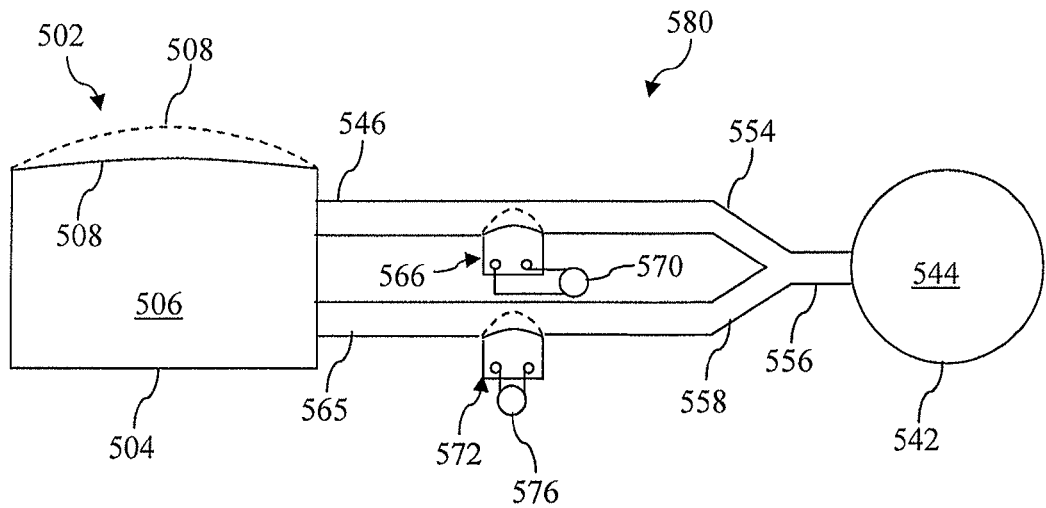
FIG. 7 is a diagrammatic schematic view of a valve system according to another embodiment of the present disclosure.

Referring now to FIG. 7, shown therein is a diagrammatic schematic view of a valve system 580 according to another embodiment of the present disclosure. In that regard, valve system 580 is similar in many respects to valve system 540 described above, but the valve system 580 does not include check valves 548, 552, 562, and 564. Rather, the valve system 580 relies upon a nozzle/diffuser arrangement for the fluid channels associated with the bubble valves 566 and 572 to provide the desired directional fluid flows. It is understood that, in other embodiments, one or more check valves (as described above) are utilized in combination with the nozzle/diffuser arrangement of the present embodiment. In some specific embodiments, a single one-way check valve is associated with each of the bubble valves 566, 572 in addition to the nozzle/diffuser arrangement.

As shown, the valve system 580 includes an adjustable valve 502 similar to that of valve systems 500 and 540. The adjustable valve 502 is comprised of a housing 504 that defines a cavity 506 that contains fluid. A membrane or diaphragm 508 is coupled to the housing 504 such that the diaphragm defines an upper boundary of the cavity 506. In that regard, the diaphragm 508 is formed of a material that is more flexible than the material forming the housing 504 such that the diaphragm 508 is movable between different positions based upon the amount of fluid and/or pressure within the cavity 506. As the amount of fluid within the cavity 506 is increased, the pressure within the cavity increases, which results in the displacement of the diaphragm 508 away from the cavity (upwards as viewed in FIG. 6). An exemplary displaced position of the diaphragm 508 corresponding to an increased amount of fluid and pressure within cavity 506 is illustrated in phantom.

In order to control the amount of fluid within the cavity 506 and, thereby, the relative position of the diaphragm 508, the adjustable valve 502 is in communication with a fluid reservoir 542. The fluid reservoir 542 includes a housing that defines a cavity 544 that also contains fluid. In the present embodiment, the housing of the fluid reservoir 542 is formed of a relatively flexible material such that the housing is configured to inflate and deflate depending on the amount of fluid received within cavity 544. Accordingly, the housing defines a varying volume for cavity 544 during use.

The cavity 506 of the adjustable valve 502 is in fluid communication with the cavity 544 of the fluid reservoir 542. This allows a flow of fluid between the cavities 506 and 544 such that a desired amount of fluid is held within cavity 506 in order to maintain the diaphragm 508 in a desired position. In that regard, a fluid channel 546 extends from cavity 506 to a fluid channel 554 that extends to a fluid channel 556 that extends from cavity 544. In that regard, the fluid channels 546, 554, and 556 define a single continuous channel in some instances. In the illustrated embodiment, fluid channel 556 serves as both an egress and ingress fluid channel for cavity 544. In other embodiments, two separate fluid channels are provided, one for egress of fluid from cavity 544 and one for ingress of fluid to cavity 544. In the illustrated embodiment, fluid channel 556 is also in fluid communication with fluid channel 558 that extends to a fluid channel 565 that is in fluid communication with cavity 506. In that regard, the fluid channels 556, 558, and 565 define a single continuous channel in some instances.

The valve system 580 also includes a bubble chamber 566 that is in communication with fluid channel 546. More specifically, a flexible membrane or diaphragm of the bubble chamber is in communication with the fluid channel 546. In that regard, the diaphragm can be selectively moved between positions that occupy varying amounts of the volume of the fluid channel. The particular range of fluid channel occupations provided by the diaphragm can be selected for particular uses and may include any subset of fluid channel occupations between 0% and 100% occupation. Two exemplary positions of the diaphragm are shown in FIG. 7 (an increased occupation position is shown in phantom).

A voltage source 570 is in electrical communication with a fluid within the bubble chamber 566. More specifically, electrodes coupled to the voltage source 570 are positioned in electrical communication with the fluid within the bubble chamber. In use, a voltage is applied across the electrodes in order to cause the formation of bubbles within the bubble chamber 566. Since the volume of the resulting gases is greater than the corresponding volume of the liquid that produces the gases, the diaphragm of the bubble chamber will be displaced upward, as viewed in FIG. 7. As the diaphragm is displaced upward it will occupy a greater amount of the volume of the fluid channel 546, which will force the fluid within fluid channel 546 towards cavity 544. In that regard, the structural arrangement of the fluid channel 546 ensures that fluid flows only the direction away from cavity 506 and towards cavity 544 as the diaphragm increases the amount of occupation of fluid channel 546. An example of such a structural arrangement is described below with respect to FIGS. 8 and 9. In that regard, in some instances the structural arrangement is a nozzle/diffuser arrangement that promotes fluid flow in a particular direction.

As the gases within bubble chamber 566 recombine (i.e., return to a liquid state with a reduced volume) the diaphragm will be displaced downward, as viewed in FIG. 7. In some instances, reversing the voltage applied by the electrodes of the voltage source 570 speeds up the recombination process. As the diaphragm is displaced downward it will occupy a lesser amount of the volume of the fluid channel 546, which will create a negative gauge pressure within fluid channel 546 causing fluid to flow from cavity 506 into fluid channel 546 towards cavity 544. Again, the structural arrangement of the fluid channel 546 ensures that fluid flows only the direction away from cavity 506 and towards cavity 544 as the diaphragm decreases the amount of occupation of fluid channel 546. While the operation of bubble chamber 566 has been described in terms of electrolysis, other types of chemical reactions, thermal nucleation, and/or mechanical arrangements (like a piston or other moving part) may be used to change the position of diaphragm.

The valve system 580 also includes a bubble chamber 572 that is in communication with fluid channel 565. More specifically, a flexible membrane or diaphragm of the bubble chamber 572 is in communication with the fluid channel 565. In that regard, the diaphragm can be selectively moved between positions that occupy varying amounts of the volume of the fluid channel. The particular range of fluid channel occupations provided by the diaphragm can be selected for particular uses and may include any subset of fluid channel occupations between 0% and 100% occupation. Two exemplary positions of the diaphragm are shown in FIG. 7 (an increased occupation position is shown in phantom).

A voltage source 576 is in electrical communication with a fluid within the bubble chamber 572. More specifically, electrodes coupled to the voltage source 576 are positioned in electrical communication with the fluid within bubble chamber. In use, a voltage is applied across the electrodes in order to cause the formation of bubbles within the bubble chamber 572. Since the volume of the resulting gases is greater than the corresponding volume of the liquid that produces the gases, the diaphragm of the bubble chamber will be displaced upward, as viewed in FIG. 7. As the diaphragm is displaced upward it will occupy a greater amount of the volume of the fluid channel 565, which will force the fluid within fluid channel 565 towards cavity 506. In that regard, the structural arrangement of the fluid channel 565 ensures that fluid flows only the direction away from cavity 544 and towards cavity 506 as the diaphragm increases the amount of occupation of fluid channel 565. An example of such a structural arrangement is described below with respect to FIGS. 8 and 9. In that regard, in some instances the structural arrangement is a nozzle/diffuser arrangement that promotes fluid flow in a particular direction.

As the gases within bubble chamber 572 recombine (i.e., return to a liquid state with a reduced volume) the diaphragm will be displaced downward, as viewed in FIG. 7. In some instances, reversing the voltage applied by the electrodes of the voltage source 576 speeds up the recombination process. As the diaphragm is displaced downward it will occupy a lesser amount of the volume of the fluid channel 565, which will create a negative gauge pressure within fluid channel 565 causing fluid to flow from cavity 544 into fluid channels 556, 558, and 565 towards cavity 506. Again, the structural arrangement of the fluid channel 565 ensures that fluid flows only the direction away from cavity 544 and towards cavity 506 as the diaphragm decreases the amount of occupation of fluid channel. While the operation of bubble chamber 572 has been described in terms of electrolysis, other types of chemical reactions, thermal nucleation, and/or mechanical arrangements (like a piston or other moving part) may be used to change the position of diaphragm.

By coordinating control of the bubble chambers 566 and 572, the valve system 580 can be utilized to selectively move the diaphragm 508 of valve 502 between positions that obstruct fluid flow through an adjacent lumen or fluid channel (See, for example, FIGS. 26 and 27). As discussed above with respect to valve system 500, the ability of the diaphragm 508 to be displaced allows for a variable level of flow restriction and/or pumping through the lumen or fluid channel by the varying how far into the lumen or fluid channel the diaphragm goes.

Figure 8:
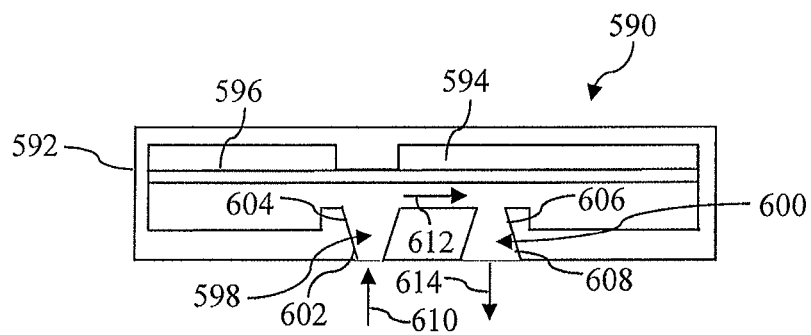
FIG. 8 is a diagrammatic cross-sectional schematic view of a valve system according to an embodiment of the present disclosure showing a diaphragm of the valve system in a first orientation.
Figure 9:
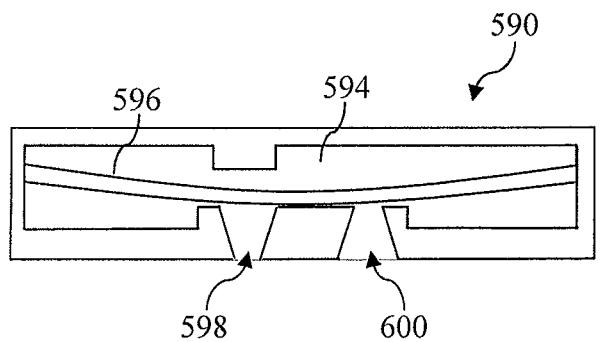
FIG. 9 is a diagrammatic cross-sectional schematic view of the valve system of FIG. 8 showing the diaphragm of the valve system in a second orientation.

Referring now to FIGS. 8 and 9, shown therein are diagrammatic cross-sectional schematic views of a pump system 590 according to an embodiment of the present disclosure. In particular, FIG. 8 shows the pump system 590 in a first orientation and FIG. 9 shows the valve system in a second orientation. More specifically, FIGS. 8 and 9 illustrate a nozzle/diffuser arrangement that facilitates directional fluid flow without the use of a check valve. Accordingly, in some instances, the nozzle/diffuser arrangement of FIGS. 8 and 9 is utilized with the bubble chambers 566 and 572 to facilitate the desired directional fluid flows between cavities 506 and 544.

As shown in FIG. 8, the pump system 590 includes a housing 592 that defines a cavity 594. The cavity 594 is bounded by a flexible membrane or diaphragm 596. In that regard, as the pressure and/or volume of fluid within cavity 594 is increased the diaphragm 596 will be displaced downward, as viewed in FIG. 8. FIG. 9 illustrates an exemplary displaced position of the diaphragm 596. Referring again to FIG. 8, the diaphragm 596 is in communication with a fluid channel that includes an opening 598 and an opening 600. In the illustrated embodiment, opening 598 serves as an inlet and opening 600 serves as an outlet. In that regard, opening 598 has a first end 602 and an opposing second end 604 where the second end 604 defines an increased cross-sectional area relative to the first end 602. In the illustrated embodiment, the opening 598 has a continuous taper from the first end 602 to the second end 604. In other embodiments, the opening 598 does not have a continuous taper, but still has ends of differing cross-sectional area. In this manner, the opening 598 defines a nozzle/diffuser. Similarly, opening 600 has a first end 606 and an opposing second end 608 where the second end 608 defines an increased cross-sectional area relative to the first end 606. In the illustrated embodiment, the opening 600 has a continuous taper from the first end 606 to the second end 608. In other embodiments, the opening 600 does not have a continuous taper, but still has ends of differing cross-sectional area. Further, in the illustrated embodiment, the opening 600 has a profile that is identical to opening 598, but oriented in the opposite direction (as viewed in FIG. 8). In other instances, the opening 600 has a different profile than opening 598. Regardless of the specific profile, the opening 600 defines a nozzle/diffuser.

Together, the openings 598 and 600 facilitate fluid flow along the path defined by arrows 610, 612, and 614. More specifically, as the diaphragm 596 is moved between a first position spaced from the openings 598, 600 (as shown in FIG. 8) and a second position closer to the openings 598, 600 (as shown in FIG. 9) the profiles of the openings 598, 600 will cause fluid to flow in the direction of arrows 610, 612, and 614. More specifically, as the diaphragm 596 transitions from the second position of FIG. 9 towards the first position of FIG. 8 (i.e. upward motion of the diaphragm as viewed in the figures), fluid will be drawn into the fluid channel through opening 598. In that regard, the expanding profile of opening 598 between its first end 602 and second end 604 provides less resistance to fluid flow than the narrowing profile of opening 600. Similarly, as the diaphragm 596 transitions from the first position of FIG. 8 towards the second position of FIG. 9 (i.e. downward motion of the diaphragm as viewed in the figures), fluid will be pushed out of the fluid channel through opening 600. In that regard, the expanding profile of opening 600 between its first end 606 and second end 608 provides less resistance to fluid flow than the narrowing profile of opening 598. In this manner, the oscillation of diaphragm 596 can be utilized to cause directional fluid flow. Accordingly, in some embodiments this structural arrangement is utilized in the context of bubble chambers of the present disclosure. For example, in some instances, the diaphragm 596 is the diaphragm of a bubble chamber and the openings 598 and 600 are portions of an associated lumen or fluid channel. In that regard, it is understood that the orientations of the openings 598 and 600 can be reversed to facilitate fluid flow in the opposite direction, if desired.

Figure 10:
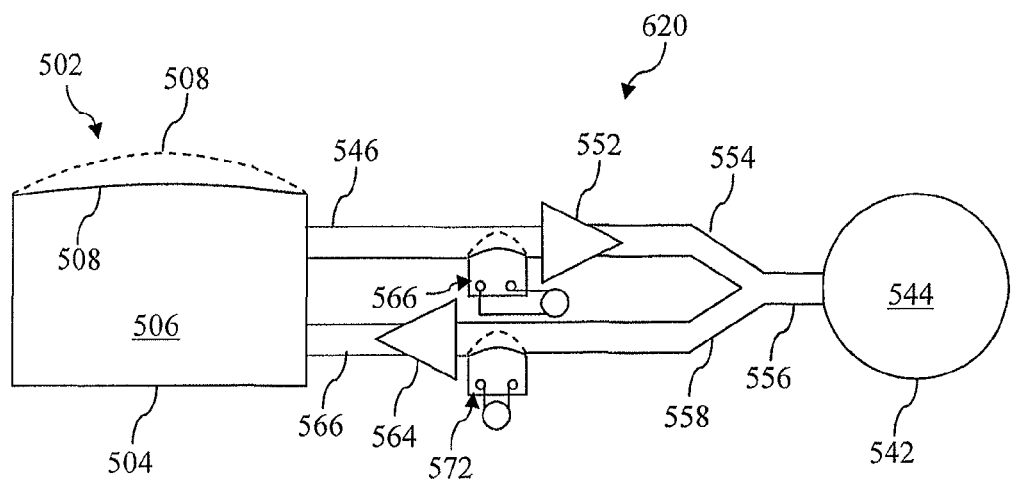
FIG. 10 is a diagrammatic schematic view of a valve system according to another embodiment of the present disclosure.

Referring now to FIG. 10, shown therein is a diagrammatic schematic view of a valve system 620 according to another embodiment of the present disclosure. In that regard, valve system 620 is similar in many respects to valve system 580 described above, but the valve system 620 includes check valves 552 and 564. In that regard, check valves 552 and 564 operate in the same manner as described above with respect to valve system 540. Further, the bubble chambers 566 and 572 are associated with nozzle/diffuser fluid channels, as described above with respect to valve systems 580 and 590. In other embodiments, however, at least one of the bubble chambers 566 and 572 is not associated with a nozzle/diffuser fluid channel.

Figure 11:
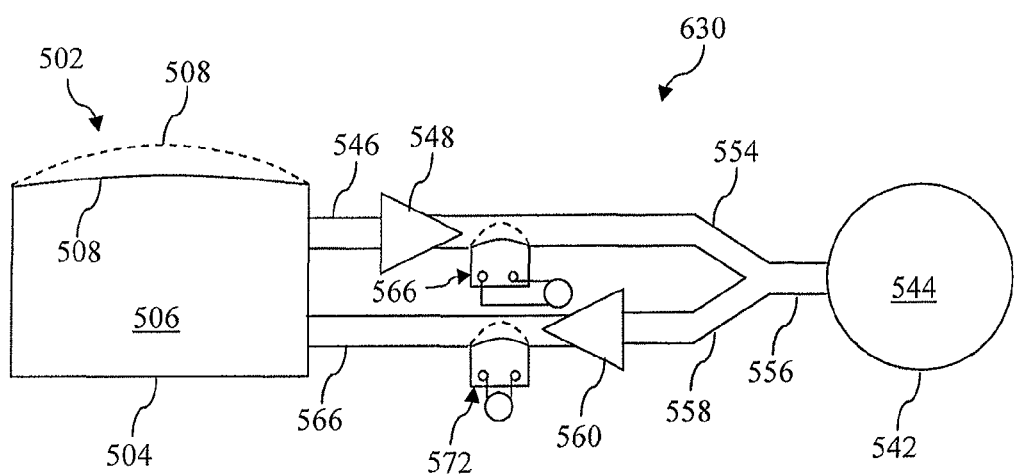
FIG. 11 is a diagrammatic schematic view of a valve system according to another embodiment of the present disclosure.

Referring now to FIG. 11, shown therein is a diagrammatic schematic view of a valve system 630 according to another embodiment of the present disclosure. In that regard, valve system 630 is similar in many respects to valve system 580 described above, but the valve system 630 includes check valves 548 and 560. In that regard, check valves 548 and 560 operate in the same manner as described above with respect to valve system 540. Further, the bubble chambers 566 and 572 are associated with nozzle/diffuser fluid channels, as described above with respect to valve systems 580 and 590. In other embodiments, however, at least one of the bubble chambers 566 and 572 is not associated with a nozzle/diffuser fluid channel.

Figure 13:
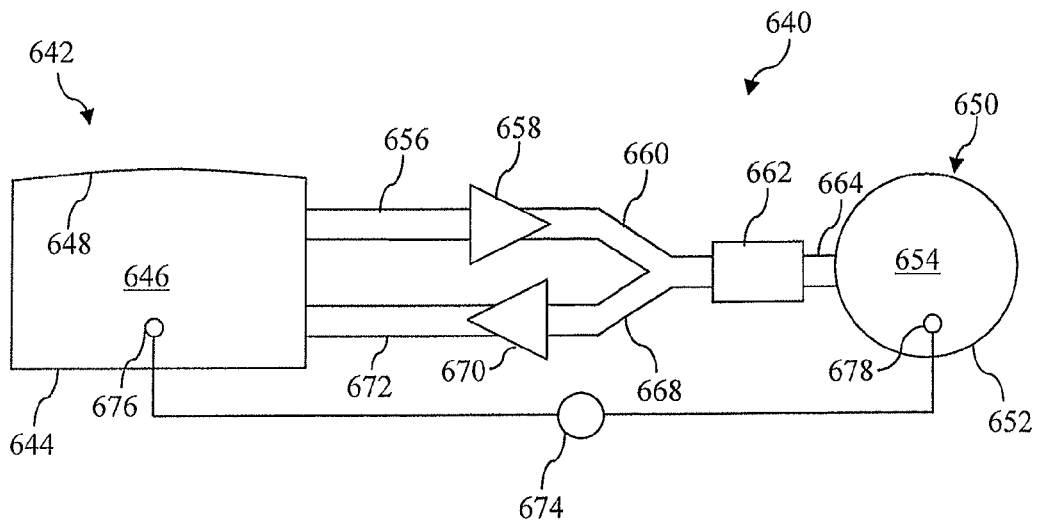
FIGS. 13-17 are sequential diagrammatic schematic views of the valve system of FIG. 12 illustrating operation of the valve system. In particular.
Figure 14:
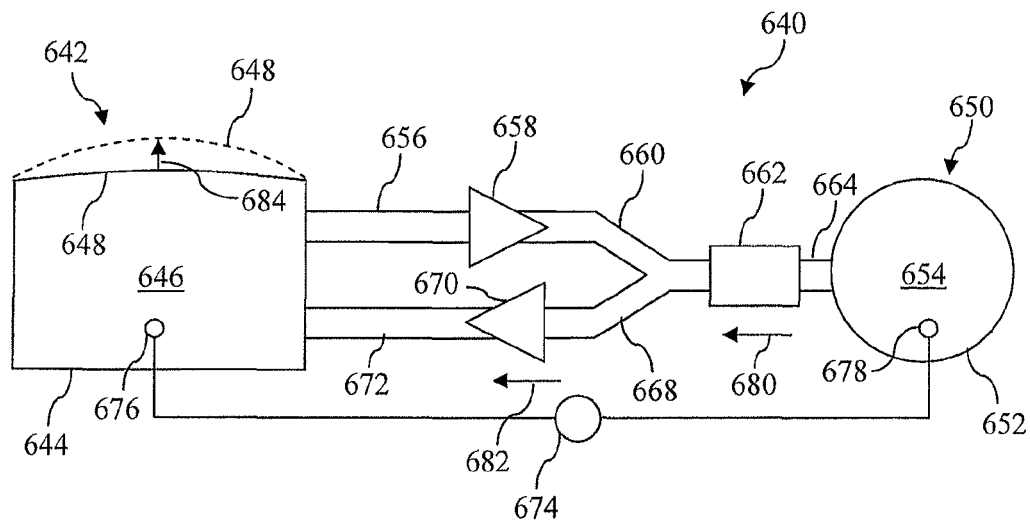
Figure 15:
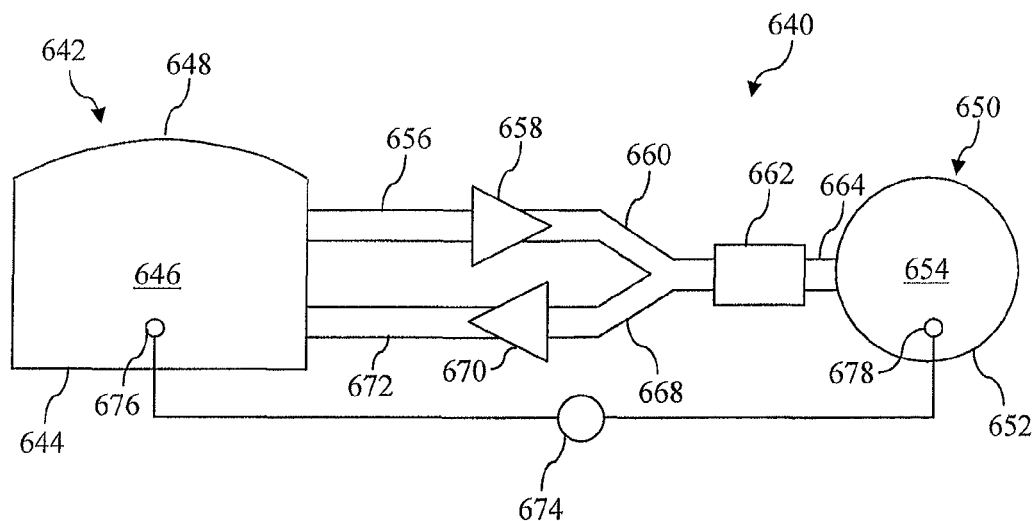
Figure 16:
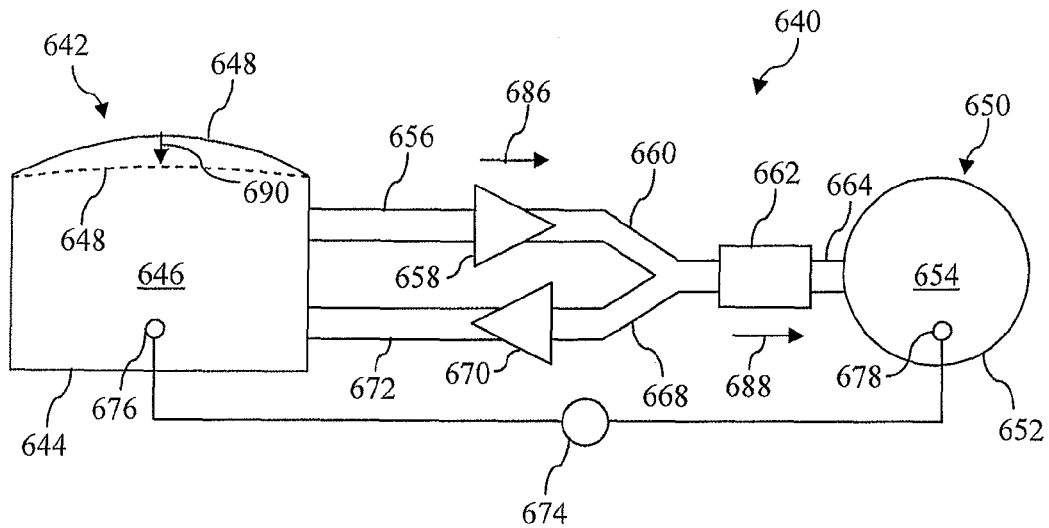
Figure 17:
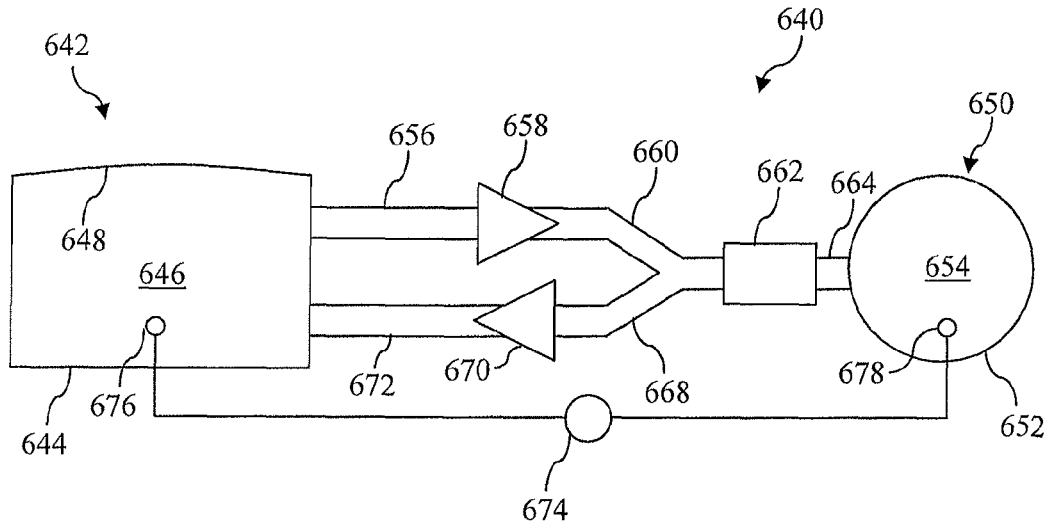

Referring now to FIGS. 12-17, shown therein are aspects of a valve system 640 according to another embodiment of the present disclosure. In that regard, FIG. 12 is a diagrammatic schematic view of the valve system 640, while FIGS. 13-17 are sequential diagrammatic schematic views of the valve system illustrating operation of the valve system. More specifically, FIG. 13 is a diagrammatic schematic view of the valve system 640 in a first orientation; FIG. 14 is a diagrammatic schematic view of the valve system showing a transition from the first orientation illustrated in FIG. 13 to a second orientation; FIG. 15 is a diagrammatic schematic view of the valve system in the second orientation; FIG. 16 is a diagrammatic schematic view of the valve system showing a transition from the second orientation illustrated in FIG. 15 to a third orientation; FIG. 17 is a diagrammatic schematic view of the valve system in the third orientation.

Referring more specifically to FIG. 12, the valve system 640 includes an adjustable valve 642. The adjustable valve 642 is comprised of a housing 644 that defines a cavity 646 that contains an electro-kinetic fluid (that is, a fluid compatible with and well-suited for electro-kinetic pumping). A membrane or diaphragm 648 is coupled to the housing 644 such that the diaphragm defines an upper boundary of the cavity 646. In that regard, the diaphragm 648 is formed of a material that is more flexible than the material forming the housing 644 such that the diaphragm 648 is movable between different positions based upon the amount of fluid within the cavity 646. In some instances, the diaphragm 648 is formed of silicone rubber, polyimide, a thin silicon membrane, Parylene, a thin silicon nitride membrane, gold, Parylene/gold/Parylene composite membranes and the like, and/or other suitable materials. As the amount of fluid within the cavity 646 is increased, the pressure within the cavity increases, which results in the displacement of the diaphragm 648 away from the cavity (upwards as viewed in FIG. 12). An exemplary displaced position of the diaphragm 648 corresponding to an increased amount of fluid and pressure within cavity 646 is illustrated in phantom. In some instances, the adjustable valve 642 is implemented as a boss valve (e.g., similar to the boss valve illustrated in FIGS. 18-20 and described below).

In order to control the amount of fluid within the cavity 646 and, thereby, the relative position of the diaphragm 648, the adjustable valve 642 is in communication with an electro-kinetic fluid reservoir 650. The fluid reservoir 650 includes a housing 652 that defines a cavity 654 that also contains the electro-kinetic fluid. In the present embodiment, the housing 652 is formed of a relatively flexible material, such as Parylene, silicone rubber, thin silicon membranes, Parylene/Au/Parylene composites, polyimide, thin silicon nitride membranes, gold membranes and the like. In some instances, the housing 652 is an expandable pouch or bag. In that regard, the housing 652 is designed to inflate and deflate depending on the amount of fluid received within cavity 654. Accordingly, the housing defines a varying volume for cavity 654 during use. In some instances, the housing 652 is received within a chamber that limits inflation of the housing. In that regard, the chamber is defined by a material having an increased stiffness and/or hardness compared to the material of the housing 652, in some instances.

The cavity 646 of the adjustable valve 642 is in fluid communication with the cavity 654 of the fluid reservoir 650. This allows a flow of fluid between the cavities 646 and 654 such that a desired amount of fluid is held within cavity 646 in order to maintain the diaphragm 648 in a desired position. In that regard, a lumen 656 extends from cavity 646 to a check valve 658. Check valve 658 allows fluid flow only in the direction away from cavity 646 and towards cavity 654. That is, check valve 658 prevents fluid flow from cavity 654 towards cavity 646. A lumen 660 connects lumen 656 and check valve 658 to an electro-kinetic porous membrane 662. A lumen 664 connects the electro-kinetic porous membrane 662 to cavity 654. In that regard, in the illustrated embodiment lumen 664 serves as both an egress and ingress lumen for cavity 654.

In the illustrated embodiment, in addition to being in fluid communication with lumen 660, lumen 664 and electro-kinetic porous membrane 662 are also in fluid communication with lumen 668. Lumen 668, in turn, extends to a check valve 670. Check valve 670 allows fluid flow only in the direction away from cavity 654 and towards cavity 646. That is, check valve 670 prevents fluid flow from cavity 646 towards cavity 654. A lumen 672 connects lumen 668 and check valve 670 to cavity 646. Generally, the check valves 658, 670 can have any desired cracking pressure. As the function of the check valves is to ensure that fluid flows in a particular, any type of check valve or one way valve may be used, including, for example, a flapper or Reed valve.

In one embodiment, with the intent to maintain pressure in cavity 646 when desired, check valve 658 has a non-zero cracking pressure approximately equal to the pressure required to maintain membrane 648 in the maximum outward position meaning valve 642 is fully closed. For example, such a pressure might be 100 mmHg with a tolerance of about 5 mmHg. In this way pressure in cavity 646 is maintained with zero energy applied to the system (i.e. no power consumed by voltage supply 674) and thus the height of diaphragm 648 is maintained. If the pressure in cavity 646 is to be reduced (diaphragm 648 lowered and thus valve 642 opened), then activation voltage supply 674 creates a pressure gradient forcing fluid from cavity 646 to cavity 654 through check valve 658 via flow channels 656, 660. Conversely, if it is desired to raise diaphragm 648, then activation voltage supply 674 creates a pressure gradient forcing fluid from cavity 654 to cavity 646 through check valve 670 via fluid channels 668, 672. In this instance, check valve 670 has a cracking pressure near zero (for example, 0.1 mmHg or lower).

The valve system 640 also includes a voltage source 674 that is in electrical communication with the electro-kinetic fluid within cavities 646 and 654. More specifically, electrodes 676 and 678 that are connected to the voltage source 674 are positioned in electrical communication with the electro-kinetic fluid within the cavities 646 and 654. While the electrodes 676 and 678 are shown as being positioned within cavities 646 and 654, respectively, in other embodiments one or more of the electrodes is outside of the cavities. Generally, however, electrodes are positioned on either side of the electro-kinetic porous membrane 662. For example, in one embodiment, the electrodes 676 and 678 are both positioned in fluid channel 664 where electrode 67 is positioned between fluid channels 660, 668 and electro-kinetic porous membrane 662 and electrode 678 is positioned in between electro-kinetic porous membrane 662 and cavity 654. The electrodes 532, 534 are formed of a conductive material, such as platinum (Pt), gold (Au), silver (Ag), silver chloride (AgCl), iridium with a coating of oxide ($IrO_2$), carbon (e.g., thick-film, nano-porous, and/or "aerogel" type carbon as used in super capacitors), copper, and/or other conductive materials. In use, a voltage is applied across electrodes 676, 678 in order to cause the flow of fluid across electro-kinetic porous membrane 662. In that regard, the electro-kinetic fluid received within the valve system 640 is generally an aqueous solution with a neutral pH level. In some instances, for efficient pumping, the pH of the electro-kinetic fluid is chosen such that the zeta potential of the EK pump material selected is at a maximum. Final trade-off could be driven by biocompatibility (e.g. pH neutral to ocular fluids). Typical ranges are pH 4-8 with a buffer capacity of 5-50 mM. The electro-kinetic fluid is non-toxic with a low to medium conductivity. In one instance, this fluid is deionized water.

The resulting electric field applied to the electro-kinetic fluid by the electrodes 676, 678 is utilized to drive the fluid through the porous membrane 662. In that regard, the relationship between pressure buildup in the electro-kinetic fluid and the flow rate of the fluid depends on the strength of the applied electric field and the properties of the materials involved. In some instances, the structures of the valve system 640 are formed of glass, silica, frit material (e.g., sintered glass micro-beads), porous polymers, and/or combinations thereof. In some particular instances the structures of the valve system 640 are formed using semi-conductor and/or MEMS manufacturing techniques. In that regard, the structures are formed by interconnecting features of a plurality of material layers. Further, in some instances a porous polymer (e.g., PVDF with a 100 or 200 nm pore size) is used as the electro-kinetic porous membrane 662. In some embodiments, a suitable off-the-shelf filtration membrane is utilized as electro-kinetic porous membrane 662.

Referring now to FIGS. 13-17, operation of the valve system 640 will be described. Referring more specifically to FIG. 13, the valve system 640 is shown in a first orientation. In that regard, the diaphragm 648 is shown in a neutral position. With the valve system 640 in the first orientation, a positive voltage is applied across electrodes 676 and 678. Referring now to FIG. 14, the valve system 640 is shown transitioning from the first orientation illustrated in FIG. 13 to a second orientation. In that regard, the application of a positive voltage across the electrodes 676, 678 causes a positive electro-kinetic pressure that urges the electro-kinetic fluid from cavity 654 through the electro-kinetic porous membrane 662 (as indicated by arrow 680) and through check valve 670 (as indicated by arrow 682) into cavity 646. The one-way nature of check valve 658 prevents the flow of fluid through lumens 660 and 656 toward cavity 646. As the volume of fluid received within cavity 646 increases as a result of the fluid flow, the diaphragm 648 is displaced upward (as indicated by arrow 684) towards a fully expanded position. Once the desired position of diaphragm 648 is reached, the voltage source 674 decreases the voltage applied to the electrodes 676, 678. In some instances, the voltage source 674 is de-energized such that the applied voltage is 0.

Referring now to FIG. 15, the valve system 640 is shown in a second, expanded orientation. In some instances, the expanded orientation of FIG. 15 is a fully expanded position. The valve system 640 is configured to maintain the expanded position of diaphragm 648 without the application of a positive voltage (see above discussion in reference to FIG. 12 regarding check valve pressure and below discussion in reference to FIG. 17). In that regard, backward flow of fluid from the cavity 646 into lumens 672 and 668 is prevented by check valve 670. Further, in some embodiments the cracking pressure of the check valve 658 is greater than or approximately equal to the maximum pressure occurring within the cavity 646 that is associated with the fully expanded position of the diaphragm 648. Accordingly, regardless of the amount of displacement of the diaphragm 648, the check valve 658 will prevent the flow of fluid through lumens 656 and 660 towards cavity 654. In this manner, the valve system 640 is able to maintain the diaphragm in a fixed position without the application of voltage from the voltage source 674. Accordingly, in some instances, the valve system 640 only consumes power when moving between different settings. Once the valve system 640 reaches the desired setting, no additional power is needed to maintain the valve system in the desired position.

With the valve system 640 in the second, expanded orientation, a positive voltage may be applied across electrodes 676 and 678 to further expand the diaphragm 648 towards the fully expanded position (in the same manner described above) or a negative voltage may be applied across electrodes 676 and 678 to retract the diaphragm 648. Referring now to FIG. 16, the valve system 640 is shown transitioning from the second, expanded orientation illustrated in FIG. 15 to a third orientation with the application of a negative voltage. In that regard, the application of a negative voltage across the electrodes 676, 678 causes a negative electro-kinetic pressure (in addition to the negative pressure provided by the fluid within cavity 646) that urges the electro-kinetic fluid from cavity 646 through check valve 658 (as indicated by arrow 686) and through the electro-kinetic porous membrane 662 (as indicated by arrow 688) into cavity 654. The one-way nature of check valve 670 prevents the flow of fluid through lumens 672 and 668 toward cavity 654. As the volume of fluid received within cavity 646 decreases as a result of the fluid flow, the diaphragm 648 is displaced downward (as indicated by arrow 690) towards a third, retracted orientation. Once the desired position of diaphragm 648 is reached, the voltage source 674 increases the voltage applied through the electrodes 676, 678. In some instances, the voltage source 674 is de-energized such that the applied voltage is 0.

Referring now to FIG. 17, the valve system 640 is shown in the third, retracted orientation. In some instances, the retracted orientation of FIG. 17 is the neutral position of FIG. 13. Again, the valve system 640 is configured to maintain the retracted position of diaphragm 648 without the application of negative voltage. In that regard, flow of fluid from the cavity 654 into lumens 656 and 660 is prevented by check valve 658. Also, the fluid pressure within cavity 646 will cause valve 670 to remain closed, preventing the flow of fluid through lumens 668 and 672 towards cavity 646. In this manner, the valve system 640 is able to maintain the diaphragm in the retracted position without the application of voltage from the voltage source 674. Again, in some instances, the valve system 640 only consumes power when moving between different settings such that no additional power is needed to maintain the position of the diaphragm 648 once the valve system 640 reaches the desired setting.

In one particular embodiment, the cracking pressure of check valve 658 is approximately 100 mmHg, the pressure required to set the valve 642 at its maximum expansion state (i.e., diaphragm 648 displaced upwards to its maximum extent) is approximately 90 mmHg, and the pressure between the check valves 658, 670 and the electro-kinetic porous membrane 662 is approximately −20 mmHg when pumping fluid out of cavity 646 towards cavity 654. Accordingly, when the pressure between the check valves 658, 670 and the electro-kinetic porous membrane 662 is driven to approximately −20 mmHg using voltage source 674 (as discussed below) while the valve 642 is in its maximum expansion state, the pressure difference across valve 658 will be approximately 110 mmHg, which exceeds the 100 mmHg cracking pressure of the valve 658. Accordingly, fluid will flow through the valve 658 until the pressure difference across the valve 658 dips below the cracking pressure of 100 mmHg for the valve. It is understood that these exemplary pressures are for illustration of the function of the system and are not limiting in any way. Rather, it is understood that a wide range of cracking pressures, maximum expansion pressures, and/or driving pressures are used within the context of the present disclosure. Further, it is also understood that similar pressure concepts are utilized to cause fluid to flow through valve 670 towards cavity 646. In that regard, the cracking pressure of valve 670 is less than pressure required to set the valve 642 at its maximum expansion state (i.e., diaphragm 648 displaced upwards to its maximum extent) and is less than the cracking pressure of valve 658, in some embodiments. In one instance, check valve 670 has a cracking pressure near zero (for example, 0.1 mmHg or lower).

The valve system 640 can be selectively moved between positions that obstruct fluid flow through an adjacent lumen (See, for example, FIGS. 26 and 27) with selective application of positive and/or negative voltages to the electro-kinetic fluid. In that regard, the ability of the diaphragm 648 to be displaced allows for a variable level of flow restriction through the lumen by the varying how far into the lumen the diaphragm goes. In some instances, the diaphragm 648 is movable between a position that does not block the lumen at all (0% blockage), a position that blocks the lumen completely (100% blockage), and positions therebetween that partially block the lumen (0.01-99.9% blockage). The particular range of lumen blockages provided by the valve system 640 can be selected for particular uses and may include any subset of lumen blockages between 0% and 100% blockage. In use, the valve system 640 can restrict the amount of aqueous that enters the drainage location and exits the anterior chamber. In some instances, the valve system 640 controls the aqueous flow based on readings from pressure sensor (s), such as P1, P2, and P3, as described above. Controlling aqueous flow can reduce the chances of hypotony after filtration surgery, maintain a suitable IOP, and/or control the amount of stagnant aqueous in the drainage location. When the drainage location is a subconjunctival bleb, controlling the amount of stagnant aqueous in the bleb can help maintain proper bleb morphology and reduce the amount of fibrosis. Too much stagnant aqueous in a bleb can lead to fibrosis. It has been postulated that fibroblasts form in stagnant aqueous and that too much tension on the bleb wall (i.e., too high a pressure in the bleb) can lead to bleb failure. Accordingly, the use of valves and valve systems of the present disclosure, including valve system 640, can lead to proper bleb maintenance, which decreases the chances of these deleterious side effects. In some instances, the diaphragm 648 is repeatedly transitioned between an open position and a closed position to cause a flow of fluid through an associated lumen (i.e., the diaphragm is utilized to pump fluid). In this manner, the valve system 640 can be utilized as a pump.

Figure 18:
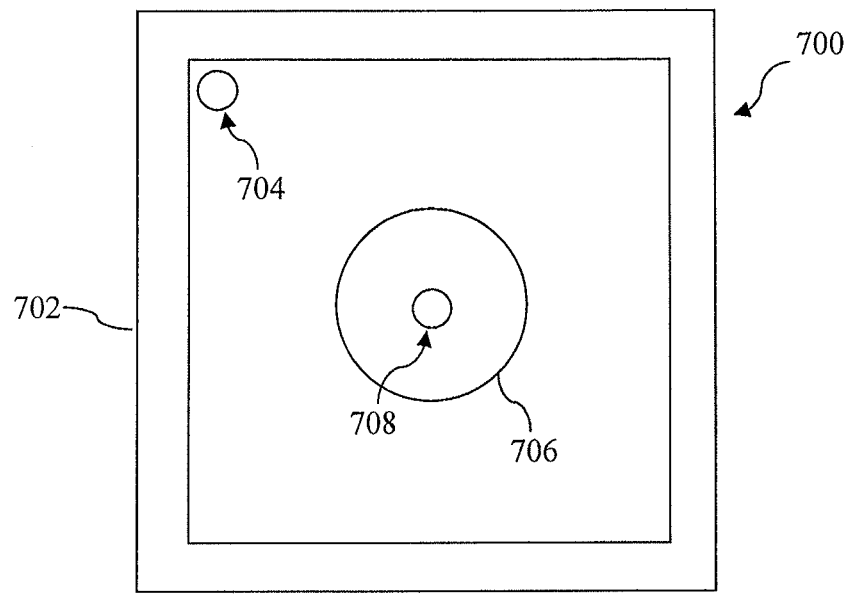
FIG. 18 is a diagrammatic top view of a boss valve system according to an embodiment of the present disclosure.
Figure 19:
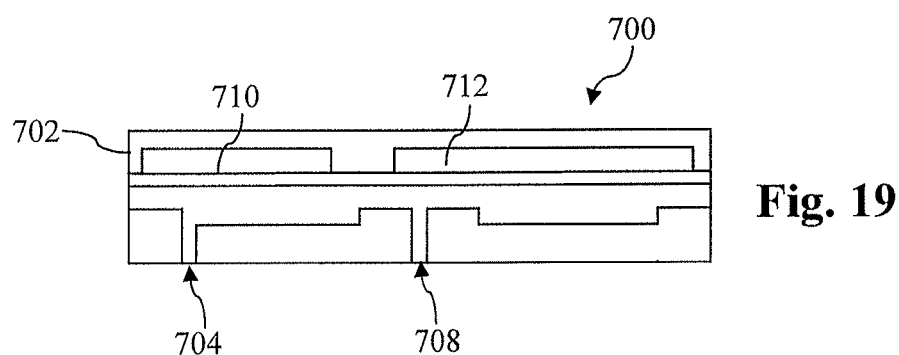
FIG. 19 is a diagrammatic cross-sectional side view of the boss valve system of FIG. 18 showing a diaphragm of the boss valve system in a first orientation.
Figure 20:
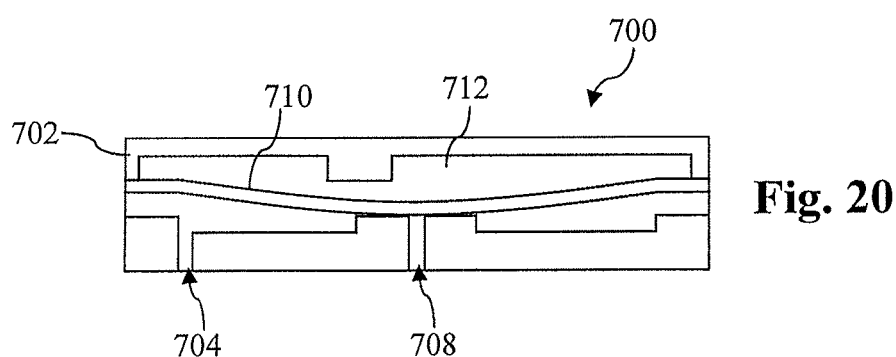
FIG. 20 is a diagrammatic cross-sectional side view of the boss valve system of FIG. 18 similar to that of FIG. 19, but showing the diaphragm of the boss valve system in a second orientation.

Referring now to FIGS. 18-20, shown therein are aspects of a boss valve system 700 according to an embodiment of the present disclosure. More specifically, FIG. 18 is a diagrammatic top view of the boss valve system 700; FIG. 19 is a diagrammatic cross-sectional side view of the boss valve system in a first orientation; and FIG. 20 is a diagrammatic cross-sectional side view of the boss valve system similar to that of FIG. 19, but showing the boss valve system in a second orientation. As shown in FIG. 18, the boss valve system 700 includes a housing 702 having an opening 704, a boss 706, and an opening 708. In some embodiments, the openings 704, 708 have a diameter between about 100 to 1,000 micrometers, while the boss 706 has a diameter between about 110 to 4,000 micrometers.

Referring now to FIGS. 19 and 20, the boss 706 includes a diaphragm 710 positioned adjacent a chamber 712. In that regard, in some instances the diaphragm 710 and chamber 712 are similar to or identical to the diaphragms and associated cavities described above with respect to previous valve systems. In that regard, it is understood that any of previously described valve systems may be implemented in boss valve system similar to that of FIGS. 18-20 in some embodiments. In some embodiments, the diaphragm or membrane 710 has a diameter between about 500 to 5,000 micrometers a thickness between about 0.1 to 15 micrometers and center deflection between its most expanded position and its most retracted position between about 10 to 250 micrometers.

As shown in FIGS. 19 and 20, the chamber 712 is bounded by the diaphragm 710 such that as the pressure and/or volume of fluid within chamber 712 are increased the diaphragm 710 will be displaced in a downward direction in the orientation shown in FIG. 19. In that regard, FIG. 20 illustrates an exemplary displaced position of the diaphragm 710. The diaphragm 710 is in communication with a fluid channel that includes openings 704 and 708. In the illustrated embodiment, opening 708 serves as an inlet and opening 704 serves as an outlet. In some instances, one or both of the openings 704, 708 define a nozzle/diffuser structure to facilitate the directional flow of fluid through the fluid channel. As the diaphragm 710 is moved between a first position spaced from the opening 708 (as shown in FIG. 19) and a second position closer to the opening 708 (as shown in FIG. 20) fluid will flow through the fluid channel defined by the housing. More specifically, as the diaphragm 710 transitions from the second position of FIG. 20 towards the first position of FIG. 19 (i.e. upward motion of the diaphragm as viewed in the figures), fluid will be drawn into the fluid channel through opening 708. Similarly, as the diaphragm 710 transitions from the first position of FIG. 19 towards the second position of FIG. 20 (i.e. downward motion of the diaphragm as viewed in the figures), fluid will be pushed out of the fluid channel through opening 704. In this manner, the movement of diaphragm 710, which is oscillatory in some instances, can be utilized to cause directional fluid flow. Generally, the position of the diaphragm 710 relative to opening 708 can be adjusted to control the amount of fluid flowing through the fluid channel. In that regard, the diaphragm 710 is movable between a position that does not block the fluid channel at all (0% blockage), a position that blocks the fluid channel completely (100% blockage), and positions therebetween that partially block the fluid channel (0.01-99.9% blockage).

Figure 21A:
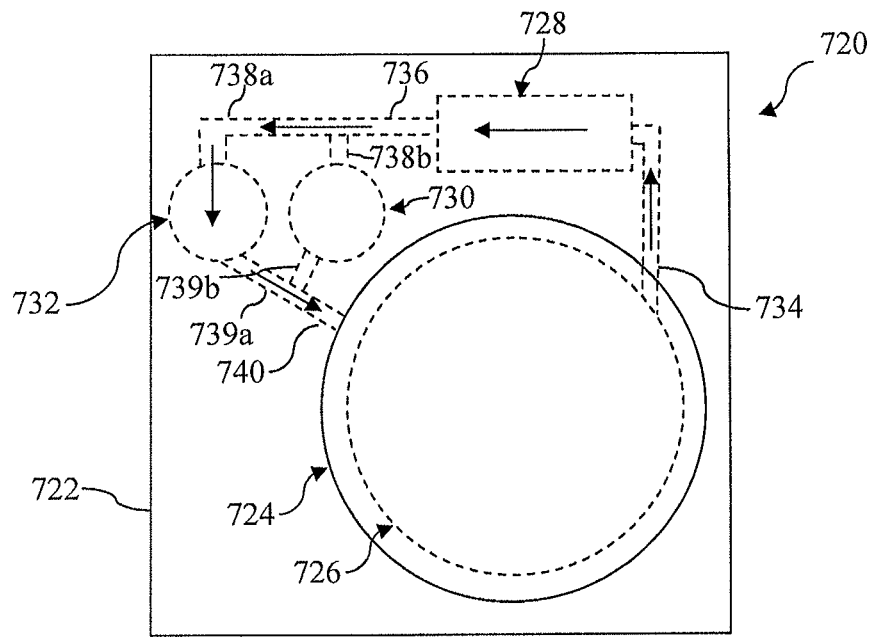
FIG. 21a is a diagrammatic top view of a valve system according to another embodiment of the present disclosure illustrating fluid flow into a cavity adjacent a diaphragm.
Figure 21B:
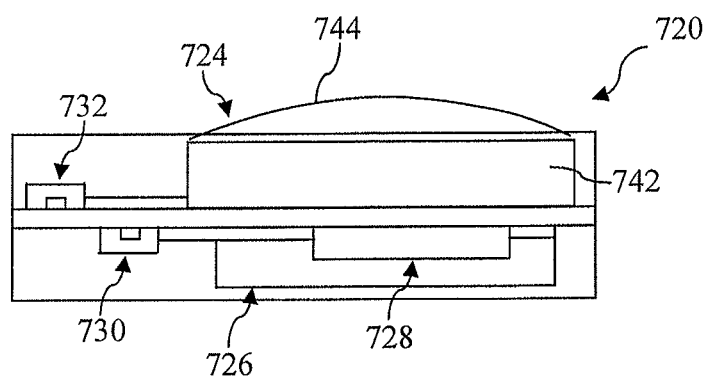
FIG. 21b is a diagrammatic cross-sectional side view of the valve system of FIG. 21a, showing the diaphragm of the valve system in a first orientation associated with fluid flow into the cavity.
Figure 22A:
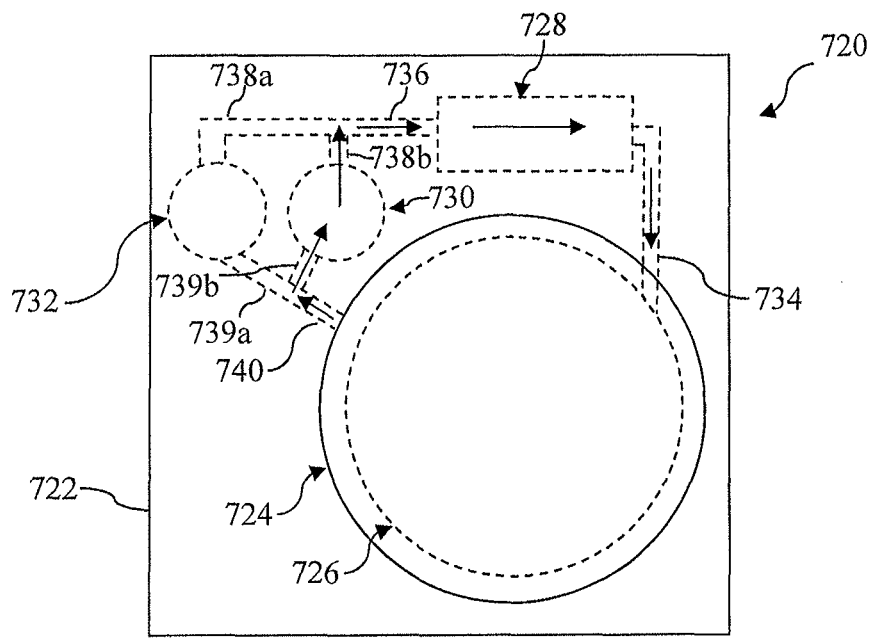
FIG. 22a is a diagrammatic top view of the valve system FIGS. 21a and 21b illustrating fluid flow out of the cavity and into a fluid reservoir.
Figure 22B:
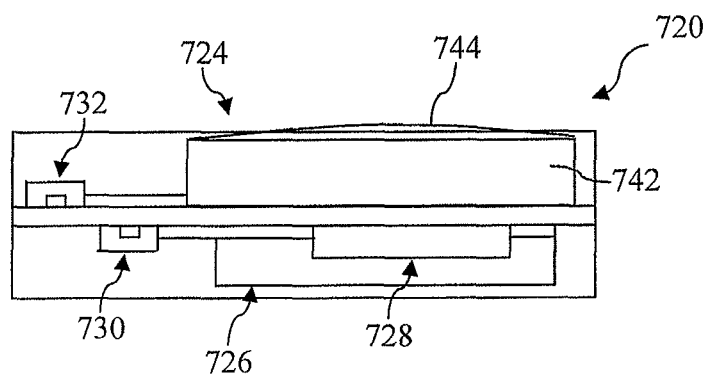
FIG. 22b is a diagrammatic cross-sectional side view of the valve system of FIG. 22a, showing the diaphragm of the valve system in a second orientation associated with fluid flow out of the cavity and into the fluid reservoir.

Referring now to FIGS. 21a, 21b, 22a, and 22b, shown therein are aspects of a valve system 720 according to another embodiment of the present disclosure. In that regard, FIG. 21a is a diagrammatic top view of the valve system 720 illustrating fluid flow in a first direction; FIG. 21b is a diagrammatic cross-sectional side view of the valve system associated with fluid flow in the first direction; FIG. 22a is a diagrammatic top view of the valve system illustrating fluid flow in a second direction; and FIG. 22b is a diagrammatic cross-sectional side view of the valve system associated with fluid flow in the second direction.

As shown, the valve system 720 includes a housing 722 that contains an adjustable valve 724, a fluid reservoir 726, an electro-kinetic membrane 728, a check valve 730, and a check valve 732. In that regard, the valve system 720 is an exemplary structural implementation of valve system 640 discussed above with respect to a schematic diagram. For example, adjustable valve 724 may be similar to valve 642, fluid reservoir 726 may be similar to fluid reservoir 650, electro-kinetic membrane 728 may be similar to electro-kinetic porous membrane 662, and check valves 730 and 732 may be similar to check valves 658 and 670. In that regard, fluid channels 734, 736, 738a, 738b, 739a, 739b, and 740 interconnect the adjustable valve 724 and the fluid reservoir 726 through the electro-kinetic membrane 728 and check valves 730, 732. It is understood that the illustrated fluid channels 734, 736, 738a, 738b, 739a, 739b, and 740 are representative of the connections between the components and, therefore, may include multiple lumens and/or channels in some instances.

Accordingly, fluid can be moved through the fluid channels between the fluid reservoir 726 and a chamber 742 of the valve 724 to adjust the relative position of a flexible membrane 744 of the valve. In that regard, FIG. 21b shows the flexible membrane 744 in an expanded position, while FIG. 22b shows the flexible membrane in a retracted position. Though not explicitly shown, it is understood that valve system 720 includes electrodes in communication with the fluid within the fluid reservoir 726 and the chamber 742 of valve 724. In that regard, the electrodes may be formed within the fluid reservoir 726 and the chamber 742 during manufacturing.

In that regard, the valve systems of the present invention can be made using manufacturing techniques in which layers are formed, for example by undergoing one or more steps that may include deposition, patterning and etching processes, on a substrate that forms part of the housing defining and/or containing the valve system, including semiconductor and/or MEMS processing techniques. In that regard, the housing is generally flat in some embodiments. In other embodiments, the housing has a slight curvature that accommodates the curvature of the eye. Generally, the housing can be made of any of a number of different biocompatible materials, including stainless steel, silicon, and/or germanium. In some embodiments, the valve systems are manufactured such that all or substantially all of the elements of the valve system are located on, under, or embedded in a plate that extends into the drainage location in a similar manner to some currently available glaucoma drainage devices.

In FIG. 21a, flow arrows indicate the direction of liquid transfer when the flexible membrane 744 is to be raised. Electronic activation of the electro-kinetic membrane 728 provides a pressure gradient that moves fluid from fluid reservoir 726 (lower portion of chip as shown) through path 734 and the electro-kinetic membrane 728, through paths 736 and 738a, check valve 732, paths 739a and 740, and into the chamber 742 of valve 724 (upper portion of the chip as shown in FIG. 21b). Note that check valve 732 only permits flow in this direction. In FIG. 22a, flow arrows indicate the direction of liquid transfer when the flexible membrane 744 is to be lowered. Electronic activation of the electro-kinetic membrane 728 provides a pressure gradient that moves fluid from the chamber 742 of valve 724 (upper portion of the chip as shown in FIG. 22b) through paths 740 and 739b, through check valve 730, through paths 738b and 736, through the electro-kinetic membrane 728, through path 734, and into fluid reservoir 726 (lower portion of chip as shown in FIG. 22b). Note that check valve 730 only permits flow in this direction.

Figure 23:
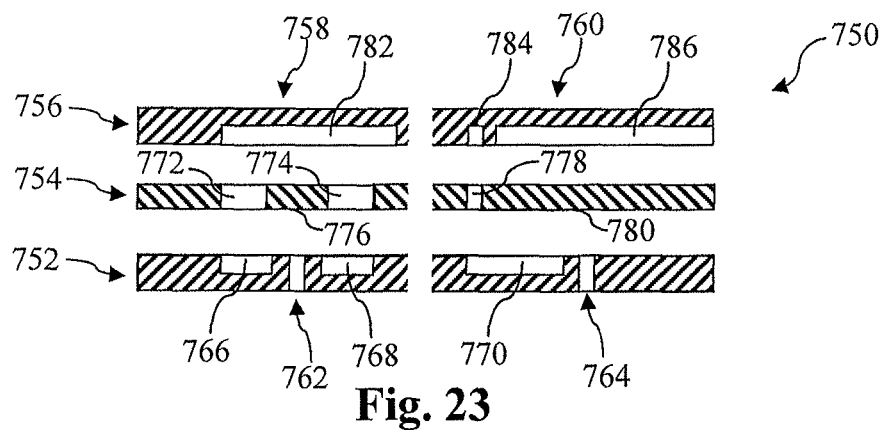
FIG. 23 is a diagrammatic cross-sectional side view of layers of a valve system according to an embodiment of the present disclosure.
Figure 24:
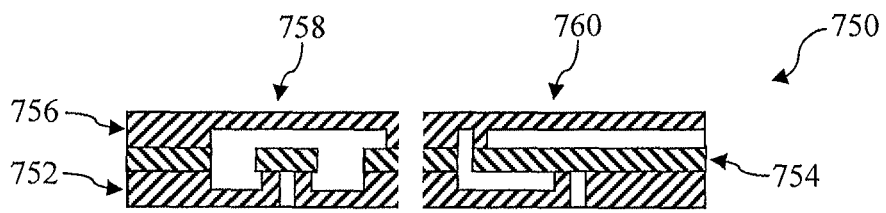
FIG. 24 is a diagrammatic cross-sectional side view of the valve system formed of the layers shown in FIG. 23.
Figure 25:
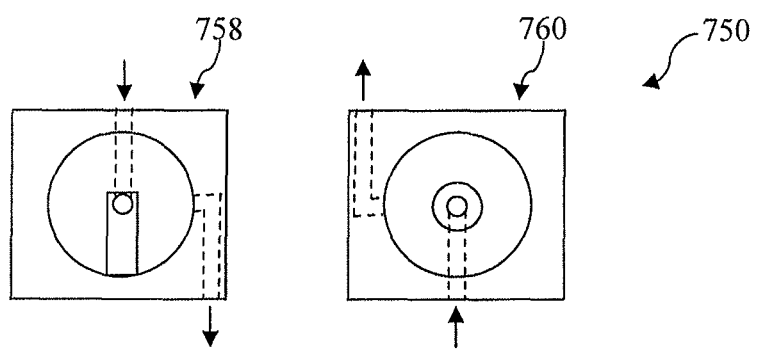
FIG. 25 is a diagrammatic top view of the valve system of FIG. 24 according to one embodiment of the present disclosure.

Referring now to FIGS. 23-25, shown therein are aspects of a valve system 750 according to another embodiment of the present disclosure. In particular, FIG. 23 is a diagrammatic cross-sectional, exploded side view of layers of the valve system 750; FIG. 24 is a diagrammatic cross-sectional, assembled side view of the valve system 750; and FIG. 25 is a diagrammatic top view of the valve system 750.

Referring more specifically to FIG. 23, the valve system 750 includes three layers, a bottom layer 752, a middle layer 754, and a top layer 756. Collectively, the layers 752, 754, and 756 define two check valves 758 and 760 in accordance with the present disclosure. In that regard, in some instances the check valves 758 and 760 are suitable for use as the check valves of the valve systems described above. In some embodiments, the valve system includes only one of the check valves 758 or 760. In other embodiments, the valve system includes two check valves, but of the same type (e.g., two valves similar to check valve 758 or two valves similar to check valve 760). In some instances, the check valves 758 and 760 are in communication with one another. In other instances, the check valves 758 and 760 are not in communication. The following description will describe the check valves 758 and 760 as being formed on the same layers 752, 754, and 756. However, it is understood that the check valves 758 and 760 are formed on different layers and/or on entirely separate chips in other embodiments.

As shown in FIGS. 23 and 24, the bottom layer 752 defines an opening 762 for valve 758 and an opening 764 for valve 760. Further, the bottom layer 752 includes recesses 766 and 768 that form a portion of a fluid channel associated with valve 758. The bottom layer 752 also includes a recess 770 that forms a portion of a fluid channel associated with valve 760. The middle layer 754 includes a pair of openings 772 and 774 that define a structure 776. In that regard, when assembled with the bottom layer 752, the structure 776 is positioned over opening 762, while openings 772 and 774 are positioned over recesses 766 and 768, respectively. The structure 776 performs as a check valve by preventing the flow of fluid down through opening 762. In that regard, the structure 776 is a cantilevered spring or flap or spider valve in some instances such that the structure 776 is displaced upwards away from opening 762 with the application of sufficient pressure.

The middle layer 754 also includes an opening 778 adjacent a structure 780. In that regard, when assembled with the bottom layer 752, the opening 778 is positioned over recess 770 to define a portion of the fluid channel while structure 780 is positioned over opening 764. In that regard, structure 780 performs as a check valve by preventing the flow of fluid down through opening 764. In that regard, in some instances the structure 780 is a flexible membrane that is displaceable upwards away from the opening 764 with the application of sufficient pressure. In some instances, the use of a flexible membrane in combination with the spring/flap structure allows the two check valves 758 and 760 to be formed with a single middle layer. In contrast, where two spring/flap structures are used, in some instances two middle layers are necessary. In this exemplary embodiment, check valve 758 is shown as a cantilevered spring valve, while check valve 760 is shown as a flexible membrane. While the valves 758 and 760 have been described as having different structures (e.g., cantilevered versus membrane), it is understood that each of the valves 758 and 760 may have any suitable structure, including the same structure as the other valve.

The upper layer 756 includes a recess 782, a recess 784, and a recess 786. In that regard, when assembled with the middle layer 754, the recess 782 is positioned over openings 772 and 774 as well as structure 776. Accordingly, the recess 782 defines a portion of the fluid channel and also provides space to allow the deflection or displacement of the structure 776 upwards away from the opening 762. Also, when assembled with the middle layer 754, the recess 784 is at least partially positioned over opening 778 to define a portion of the fluid channel associated with valve 760. Further, recess 786 is positioned over structure 780. In that regard, the recess 786 provides space to allow the displacement of the structure 780 upwards away from the opening 764. For check valves 758, flow enters opening 762 and exits via recess 782. Similarly, for check valve 760, flow enters opening 764 and exits via recess 784.

As shown in FIGS. 24 and 25, when the layers 752, 754, and 756 are assembled the valve system 750 forms the two check valves 758 and 760. In that regard, check valve 758 generally allows fluid flow in a direction opposite to the direction of fluid flow allowed by check valve 760, as indicated by the fluid flow arrows. Generally, the recesses and openings within the layers 752, 754, and 756 may be formed using any suitable manufacturing techniques. In some particular instances, the recesses and openings are formed by etching a substrate (e.g., semiconductor (such as silicon and/or germanium), glass, polymeric, and/or other suitable substrate material). In that regard, it is understood that the three-layer layout of FIGS. 23 and 24 is provided for exemplary purposes only and in no way limits the number of layers that may be utilized to form the valve systems of the present disclosure. Generally, any number of layers may be utilized to form a valve. However, in some instances it is desirable to keep the number of layers to a minimum in order to reduce the overall size and/or thickness of the resulting device. Further, it is understood that where a valve system includes multiple valves that each of the valves may be formed using the same or a different number layers as another of the valves.

Referring now to FIGS. 26 and 27, shown therein are aspects of a valve system 800 according to another embodiment of the present disclosure. In that regard, FIG. 26 shows the valve system 800 interfacing with a lumen of a glaucoma drainage device in a first orientation, while FIG. 27 shows the valve system interfacing with the lumen of the glaucoma drainage device in a second orientation. Generally speaking, the valve system 800 represents any of the valve systems of the present disclosure that may be utilized to control the flow of fluid through a lumen or tube through the control of a displaceable membrane of the valve system. In that regard, the valve system 800 includes an adjustable valve 802. The adjustable valve 802 includes a housing 804 that defines a cavity 806 that contains a fluid. A flexible membrane or diaphragm 808 is coupled to the housing 804 such that the diaphragm defines an upper boundary of the cavity 806. In that regard, the diaphragm 808 is formed of a material that is more flexible than the material forming the housing 804 such that the diaphragm 808 is movable between different positions based upon the amount of fluid and/or pressure within the cavity 806.

In order to control the amount of fluid within the cavity 806 and, thereby, the relative position of the diaphragm 808, the adjustable valve 802 is in communication with a fluid reservoir 810. In some instances, the fluid reservoir 810 defines a constant volume reservoir. In other instances, the fluid reservoir 810 is flexible such that the volume of the reservoir changes during operation of the valve system. Generally, however, the fluid reservoir 810 contains fluid that is transferred between the fluid reservoir and the cavity 806 through fluid communication channels 812 and 814. In that regard, it is understood that the fluid communication channels 812 and 814 are one way channels in some instances. For example, in some instances channel 812 facilitates the flow of fluid from fluid reservoir 810 to cavity 806, while channel 814 facilitates the flow of fluid from cavity 806 to fluid reservoir 810. In that regard, the channels 812, 814 may include features (e.g., check valves, nozzles/diffusers, etc.) to encourage fluid flow in a particular direction and prevent fluid flow in the opposite direction.

In use, the diaphragm 808 is movable between positions that occupy varying amounts of a channel or lumen 820 of a drainage structure 822. In some instances, the drainage structure is a drainage tube of a glaucoma drainage device. In that regard, the relative position of the diaphragm 808 within the lumen 820 determines the amount of fluid flow through the drainage structure. For example, in some instances the diaphragm 808 is movable between a position that does not block the lumen at all (0% blockage), a position that blocks the lumen completely (100% blockage), and positions therebetween that partially block the lumen (0.01-99.9% blockage). The particular range of lumen blockages provided by the valve system 800 can be selected for particular uses and may include any subset of lumen blockages between 0% and 100% blockage. As shown in FIGS. 26 and 27, the diaphragm 808 is movable between a first position that occupies very little of the cross-sectional area of lumen 820 (e.g., less than 10%), as shown in FIG. 26, and a second position that occupies substantially all of the cross-sectional area of lumen 820 (e.g., more than 95%), as shown in FIG. 27. By controlling the position of the diaphragm 808 within the lumen 820, the corresponding fluid flow through the drainage structure 822 can likewise be controlled.

In use, the valve systems of the present disclosure can actively pump fluid at night while the patient is sleeping. Typically, a glaucoma patient's IOP is highest in the morning (and IOP can fluctuate during the night as well). Using an IOP sensor to control the valves/pumps of the present disclosure can help to maintain proper IOP during the night. In that regard, a patient may wear a mask or have a device nearby that provides power to the valve/pump. Accordingly, in some instances, the pump and/or valve can be operated to maintain a desirable IOP using power from the nearby external device. When the patient awakens, the valve/pump of the glaucoma drainage device can be set for daytime operation that consumes much less power. For example, active pumping can occur at night when power consumption is of little concern (i.e., when a supply of energy from an external device is provided) and minimal or no pumping can occur during the day (i.e., when a supply of energy from an external device is not provided). In one example, the pump operates while the patient sleeps until the subconjunctival bleb volume is expelled into the eye socket. During this time, the drainage area may temporarily be blocked, forcing more aqueous humor to flow via the natural outflow path until the IOP rises to a threshold value, at which time the drainage area (e.g. subconjunctival space) is re-opened. By emptying the bleb at night, the flow from the anterior chamber into the vacant bleb space during the day provides drainage with little or no back pressure, which allows for a target IOP to be set and maintained. In that regard, the valves/pumps of the present disclosure can be used to maintain the IOP at or near the target IOP.

From the above, it may be appreciated that the present disclosure provides valve systems that can be controlled by an TOP sensor system to control fluid flows within a glaucoma drainage device. In that regard, as described above, in some instances operation of the valve systems of the present disclosure facilitates a pumping of fluid from one location to another. Accordingly, in such instances the valve systems of the present disclosure may also be referred to as a pump or pump system. In some embodiments, the valve systems of the present disclosure are controlled using electrolysis and/or electro-kinetic fluid flows. Other embodiments, variations, and combinations of features will be apparent to those skilled in the art from the foregoing description and accompanying drawings. Accordingly, it is intended that the examples provided in the description and drawings be considered as exemplary only, with a true scope and spirit of the invention being indicated by the following claims.

What is claimed is:

1. A valve system for use within an ophthalmic device, the valve system comprising:
   an adjustable valve having:
      a housing defining a cavity; and
      a movable diaphragm bounding at least one side of the cavity;
   a fluid reservoir in fluid communication with the cavity of the adjustable valve;
   an actuator for controlling a flow of fluid between the fluid reservoir and the cavity of the adjustable valve, the actuator comprising a voltage source, a pair of electrodes, an actuator fluid and a bubble-generating system configured to generate bubbles by converting at least a portion of the actuator fluid to a gas, wherein one of the electrodes is positioned within the fluid reservoir and the other electrode is positioned outside of the fluid reservoir;
   a first check valve positioned between the fluid reservoir and the cavity of the adjustable valve along a first fluid passageway, the first check valve preventing fluid flow from the fluid reservoir to the cavity of the adjustable valve; and
   a second check valve positioned between the fluid reservoir and the cavity of the adjustable valve along a second fluid passageway, the second check valve preventing fluid flow from the cavity of the adjustable valve to the fluid reservoir.

2. The valve system of claim 1, wherein the pair of electrodes are positioned within the fluid reservoir.

3. The valve system of claim 1, wherein the other electrode is positioned within the cavity of the adjustable valve.

4. The valve system of claim 1, wherein the fluid reservoir is formed of a material that defines a constant volume cavity during operation.

5. The valve system of claim 1, wherein the fluid reservoir is formed of a flexible material that defines a variable volume cavity during operation.

6. The valve system of claim 1 wherein at least one of the first and second check valves is a converging pathway.

7. The valve system of claim 1 wherein at least one of the first and second check valves is a diverging pathway.

8. The valve system of claim 1, further comprising:
a first bubble chamber positioned adjacent the first fluid passageway such that a diaphragm of the first adjustable component is movable between a first position that occupies a first amount of the first fluid passageway and a second position that occupies a second amount of the first fluid passageway, the second amount being greater than the first amount.

9. The valve system of claim 8, wherein the first bubble chamber is configured to control fluid flow from the cavity of the adjustable valve to the fluid reservoir.

10. The valve system of claim 9, wherein the first check valve is positioned between the first bubble chamber and the fluid reservoir.

11. The valve system of claim 9, wherein the first check valve is positioned between the first bubble chamber and the cavity of the adjustable valve.

12. The valve system of claim 9, wherein the first check valve is positioned between the first bubble chamber and fluid reservoir and a third check valve is positioned between the first bubble chamber and the adjustable valve, the third check valve also preventing flow from the fluid reservoir to the adjustable valve.

13. The valve system of claim 8, further comprising:
a second bubble chamber positioned adjacent the second fluid passageway such that a diaphragm of the second bubble chamber is movable between a first position that occupies a first amount of the second fluid passageway and a second position that occupies a second amount of the second fluid passageway, the second amount being greater than the first amount.

14. The valve system of claim 13, wherein the second bubble chamber is configured to control fluid flow from the fluid reservoir to the cavity of the adjustable valve.

15. The valve system of claim 14, wherein the second check valve is positioned between the second bubble chamber and the cavity of the adjustable valve.

16. The valve system of claim 14, wherein the second check valve is positioned between the second bubble chamber and the fluid reservoir.

17. The valve system of claim 14, wherein the second check valve is positioned between the second bubble chamber and fluid reservoir and a third check valve is positioned between the second bubble chamber and the adjustable valve, the third check valve also preventing flow from the adjustable valve to the fluid reservoir.

18. The valve system of claim 1, wherein the valve system is configured to maintain the diaphragm in a desired position after actuation of an actuator configured to move the diaphragm has ceased.

19. The valve system of claim 1, wherein the valve system is configured to pump aqueous humor from an anterior chamber of an eye.

20. The valve system of claim 19, wherein the valve system is configured to be activated when in the vicinity of an external power source and deactivated when not in the vicinity of an external power source.

* * * * *